(12) United States Patent
Gervay-Hague et al.

(10) Patent No.: US 8,946,391 B2
(45) Date of Patent: Feb. 3, 2015

(54) CONSTRUCTION OF A MULTIVALENT SCFV THROUGH ALKYNE-AZIDE 1,3-DIPOLAR CYCLOADDITION

(75) Inventors: Jacquelyn Gervay-Hague, Davis, CA (US); Wenjun Du, St. Louis, MO (US); Sally Denardo, El Macero, CA (US); Arutselvan Natarajan, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 1173 days.

(21) Appl. No.: 12/294,227

(22) PCT Filed: Mar. 26, 2007

(86) PCT No.: PCT/US2007/064947
§ 371 (c)(1),
(2), (4) Date: Sep. 23, 2008

(87) PCT Pub. No.: WO2007/112362
PCT Pub. Date: Oct. 4, 2007

(65) Prior Publication Data
US 2009/0234105 A1    Sep. 17, 2009

Related U.S. Application Data

(60) Provisional application No. 60/785,913, filed on Mar. 24, 2006.

(51) Int. Cl.
| | | |
|---|---|---|
| *C12P 21/08* | (2006.01) | |
| *C07D 403/00* | (2006.01) | |
| *C07C 247/00* | (2006.01) | |
| *C07K 16/30* | (2006.01) | |

(52) U.S. Cl.
CPC ......... *C07K 16/3015* (2013.01); *C07K 16/3069* (2013.01); *C07K 2317/31* (2013.01); *C07K 2317/622* (2013.01)
USPC .............................. 530/387.3; 548/255; 552/1

(58) Field of Classification Search
CPC ...................... C07K 2317/622; C07K 2317/32
See application file for complete search history.

(56) References Cited

U.S. PATENT DOCUMENTS

| | | | | |
|---|---|---|---|---|
| 5,571,894 A | * | 11/1996 | Wels et al. ................. | 530/387.3 |
| 2005/0032081 A1 | | 2/2005 | Ju et al. | |
| 2006/0153860 A1 | * | 7/2006 | Cho et al. ................... | 424/185.1 |

FOREIGN PATENT DOCUMENTS

WO    WO 2006/012569 A1    2/2006

OTHER PUBLICATIONS

Todorovska et al. (J. Immunol. Methods 2001, 248:47-66).*
Natarajan et al. (Chem. Comm. DOI: 20.1039/b611636a, p. 695-697, Nov. 28, 2006).*
Sun et al. (Bioconjugate Chem. Dec. 21, 2005 17: 52-57).*
Albrecht, H. et al., "Monospecific Bivalent scFv-SH: Effects of Linker Length and Location of an Engineered Cysteine on Production, Antigen Binding Activity and Free SH Accessibility," *Journal of Immunological Methods*, 2006, vol. 310, pp. 100-116.
International Search Report mailed on Mar. 10, 2008, for PCT Application No. PCT/US07/64947 filed on Mar. 26, 2007, 2 pages.

* cited by examiner

*Primary Examiner* — Peter J Reddig
(74) *Attorney, Agent, or Firm* — Kilpatrick Townsend & Stockton LLP

(57) ABSTRACT

The present invention provides for a practical, universal and efficient method to ligate two large macromolecules (e.g., proteins) using the alkyne-azide 1,3-dipolar cycloaddition reaction to produce a conjugated macromolecule, such as a multivalent scFv. The present invention also provides for conjugate macromolecules comprising a plurality of macromolecule components cross-linked through at least one linking group comprising at least one 1,2,3-triazole moiety, wherein at least 50 percent of the macromolecule components in the conjugate macromolecule has only one site available for cross-linking.

6 Claims, 9 Drawing Sheets

Conjugation Efficiency

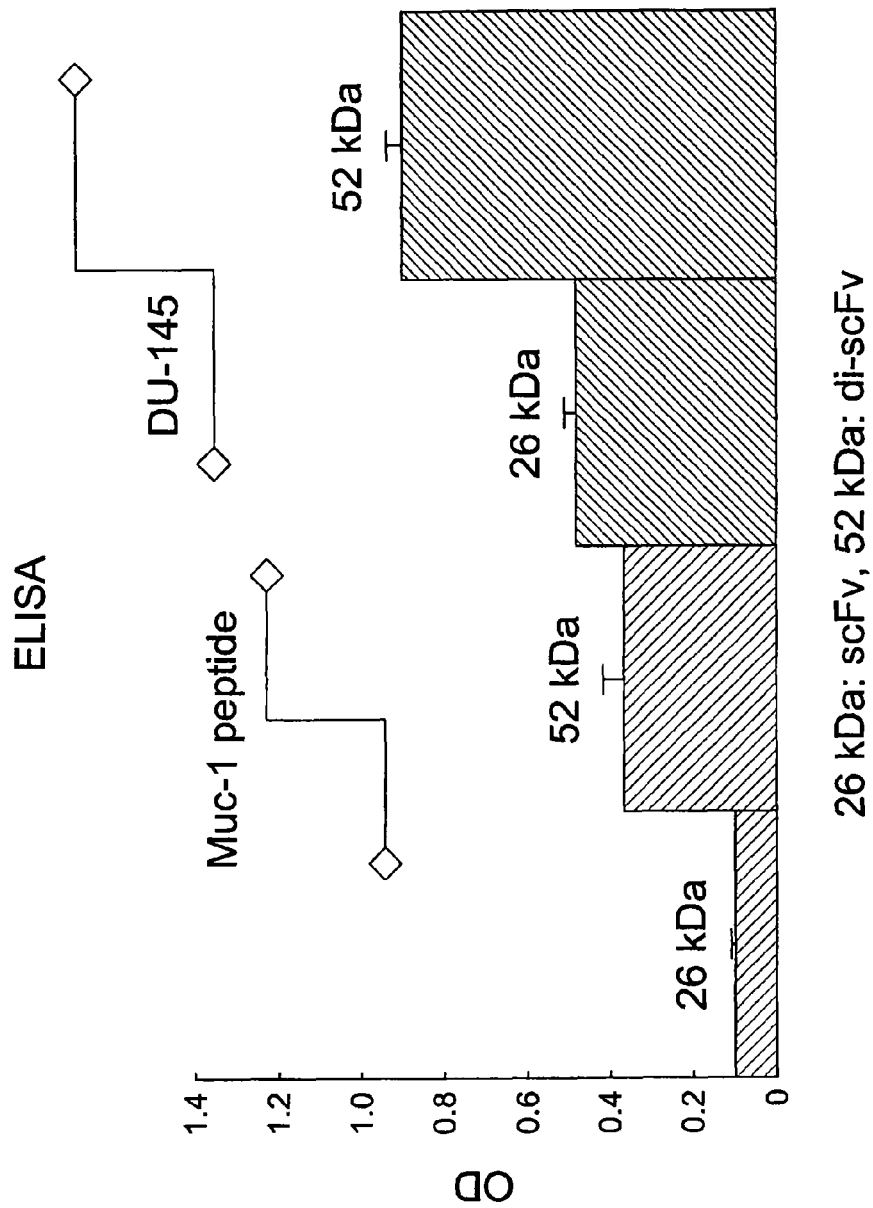

CONSTRUCTION OF A MULTIVALENT SCFV THROUGH ALKYNE-AZIDE 1,3-DIPOLAR CYCLOADDITION

CROSS-REFERENCES TO RELATED APPLICATIONS

This application claims priority to U.S. Provisional Application No. 60/785,913 filed on Mar. 24, 2006, which is incorporated herein in its entirety for all purposes.

STATEMENT AS TO RIGHTS TO INVENTIONS MADE UNDER FEDERALLY SPONSORED RESEARCH AND DEVELOPMENT

The research for this invention was partially funded by National Cancer Institute NCI Grant PO1-CA47829, and National Science Foundation CHE-0196482. The Federal government may have rights to certain aspects of this invention.

REFERENCE TO A "SEQUENCE LISTING," A TABLE, OR A COMPUTER PROGRAM LISTING APPENDIX SUBMITTED ON A COMPACT DISK

BACKGROUND OF THE INVENTION

The use of intact monoclonal antibodies (MAb), which provide superior binding specificity and affinity for a tumor-associated antigen, have been successfully applied in the area of cancer treatment and diagnosis (A). However, the large size of intact MAbs, their poor bio-distribution and long persistence in the blood pool have limited their clinical applications (B). For example, intact antibodies can exhibit specific accumulation within the tumor area. In biodistribution studies, an inhomogeneous antibody distribution with primary accumulation in the peripheral regions is noted when precisely investigating the tumor. Due to tumor necroses, inhomogeneous antigen distribution and increased interstitial tissue pressure, it is not possible to reach central portions of the tumor with intact antibody constructs. In contrast, smaller antibody fragments show rapid tumor labeling, penetrate deeper into the tumor, and also, are removed relatively rapidly from the bloodstream.

Single chain fragments (scFv) that are derived from the small binding domain of the parent MAb, offer better pharmacokinetics than intact MAbs for clinical application and can target tumor cells more efficiently (C). Single chain fragments can be efficiently engineered from bacteria, however, most engineered scFv have a monovalent structure and show decreased affinity, e.g., a short residence time on a tumor cell, and specificity as compared to their parent MAb ((C(c),D).

In order to increase the affinity and specificity of the scFv for a target antigen, the creation of a multimer, i.e., a multivalent scFv, is desirable. Multivalent antibody constructs such as multibodies (e.g, diabodies, tri-/tetrabodies), and other minibodies offer many advantages in tumor therapy. Recent constructs of multivalent scFv show $10^2$ to $10^3$ times lower off-rate and remarkable increase in binding affinity as compared to a monovalent scFv. Multivalent constructs are advantageous in tumor therapy as a result of improved pharmacokinetic properties and have been further developed for use in tumor therapy (E). They can be used as vehicles for specific accumulation of e.g. cytotoxic substances such as chemotherapeutic agents or radionuclides in a tumor. By suitably selecting the radionuclides, it is possible to destroy tumor cells over a distance of several cell diameters, so that even antigen-negative tumor cells in a tumor area can be covered and poor penetration of antibodies into solid tumors can be compensated at least in part. In spite of these many advantages for multivalent scFvs in cancer therapy, limited methods exist for producing multivalent scFvs.

Currently, most scFv is genetically engineered through bacterial or phase display libraries (E(a-d),E(f),F). In this way, scFv is composed of a heavy chain ($V_H$) and a light chain ($V_L$). The two chains are covalently linked through a polypeptide linker. A multivalent scFv can be prepared by manipulating the length of the polypeptide linker. For example, when the polypeptide linker length is less than five amino acids, the short linker precludes $V_H$-$V_L$ association but drives non-covalent dimerization to give a di-scFv. If the length is less than three amino acids, a triabody scFv could be obtained (E(a),E(c),F,G). This method is the most common used method to generate multivalent scFv in spite of the fact that folding is often distorted and specificity is reduced for this type of multivalent scFvs (H).

Alternatively, multivalent scFv can also be prepared by using multimeric affinity reagents such as polyvalent proteins or antibodies. In this way, scFv are anchored on multimers through non-covalent interactions. The main drawback to this method is poor pharmacokinetics, low throughput, and high cost. Additionally, chemical cross-linking using linkers with bi-functional groups has also been investigated but product yields of the cross-linked proteins were limited (I).

In earlier work, the inventors developed a scFv construct against tumor-associated MUC-1 antigen expressed on surface of breast cancer cells (J). In order to better target tumor cells expressing the mucin MUC-1 antigen, a multivalent scFv that can preserve specificity with improved affinity is desirable. Toward this end, the inventors constructed a di-scFv through a melamide-PEG-melamide linker by site-specific PEGylation (I(c)) in low yields (10%-30%).

Alkyne-azide 1,3-dipolar cycloaddition is a highly chemoselective, bioorthogonal (K) chemistry that has been established as an effective chemistry for covalent modification of macromolecules such as proteins (L,M), DNA (N), carbohydrate (O), even virus particle (K,P) and bacterial surfaces (Q). In these cases, a large macromolecule (e.g., protein, DNA, etc.) comprising a reactive group required for the 1,3-dipolar cycloaddition reaction, (i.e., an azide or alkyne) reacts with a small organic molecule comprising the complementary functional group required for the 1,3-dipolar cycloaddition reaction (i.e., an azide or alkyne), to form a 1,2,3-triazole to result in the ligation of a small organic molecule to the large macromolecule.

However, prior to the present invention, alkyne-azide 1,3-dipolar cycloaddition reactions have not been successfully used in the ligation of two large macromolecules each having a single site for the attachment of reactive functional groups (i.e., an azide or an alkyne). It is thought that steric hindrance and low effective concentration of the reacting functional groups are the main impediments to the reaction.

In view of the above, there remains a need in the art for a practical, universal and efficient method to ligate two large macromolecules (e.g., proteins) to produce a conjugated macromolecule, such as a multivalent scFv protein. The present invention fulfills this and other needs.

References Cited:
- A. (a) T. A. Waldmann, *Science* 1991, 252, 1657-1662; (b) M. E. Juweid, C. H. Zhang, R. D. Blumenthal, G. Hajjar, R. M. Sharkey, D. M. Goldenberg, *J. Nucl. Med.* 1999, 40, 1609-1616; (c) M. H. Sokoloff, A. Nardin, M. D. Solga, M. A. Lindorfer, W. M. Sutherland, A. J. Bankovich, H. E. Zhau, L. W. K. Chung, R. P. Taylor, *Cancer Immunol. Immunother.* 2000, 49, 551-562.
- B. (a) A. Goel, D. Colcher, J. Baranowska-Kortylewicz, S. Augustine, B. J. Booth, G. Pavlinkova, S. K. Batra, *Cancer Res.* 2000, 60, 6964-6971; (b) S. K. Batra, M. Jain, U. A. Wittel, S. C. Chauhan, D. Colcher, *Curr Opin Biotechnol.* 2002, 13, 603-608; (c) I. Blanco. R. Kawatsu, K. Harrison. P. Leichner, S. Augustine, J. Baranowska-Kortylewicz, *J. Clin. Immunol.* 1997, 17, 96-106.
- C. (a) D. E. Milenic, T. Yokota, D. R. Filpula, M. A. Finkelman, S. W. Dodd, J. F. Wood, M. Whitlow, P. Snoy, J. Schlom, *Cancer Res.* 1991, 51, 6363-6371; (b) T. Yokota, D. E. Milenic, M. Whitlow, J. Schlom, *Cancer Res.* 1992, 52, 3402-3408; (c) G. P. Adams, J. E. McCartney, M. S. Tai, H. Oppermann, J. S. Huston, W. F. Stafford, III, M. A. Bookman, I. Fand, L. L. Houston, L. M. Weiner, *Cancer Res.* 1993, 53, 4026-4034.
- D. (a) D. Colcher, D. Milenic, M. Roselli, A. Raubitschek, G. Yarranton, D. King, *Cancer Res.* 1989, 49, 1738-1745; (b) R. H. J. Begent, M. J. Verhaar, K. A. Chester, J. L. Casey, A. J. Green, M. P. Napier, L. D. Hope-Stone, N. Cushen, P. A. Keep, C. J. Johnson, R. E. Hawkins, A. J. W. Hilson, L. Robson, *Nat. Med.* 1996, 2, 979-984; (c) G. Pavlinkova, B. J. Booth, S. K. Batra, D. Colcher, *Clin. Cancer Res.* 1999, 5, 2613-2619; (d) G. Pavlinkova, G. W. Beresford, B. J. Booth, S. K. Batra, D. Colcher, *J. Nucl. Med.* 1999, 40, 1536-1546.
- E. (a) S. C. Chauhan, M. Jain, E. D. Moore, U. A. Wittel, J. Li, P. R. Gwilt, D. Colcher, S. K. Batra, *Euro. J. Nucl. Med. Mol. Im.* 2005, 32, 264-274; (b) U. A. Wittel, M. Jain, A. Goel, S. C. Chauhan, D. Colcher, S. K. Batra, *Nucl. Med. Biol.* 2005, 32, 157-164; (c) L. F. Gall, S. M. Kipriyanov, G. Moldenhauer, M. Little, *FEBS Lett.* 1999, 453, 164-168; (d) S-H. Wang, J-B. Zhang, Z-P. Zhang, Y-F. Zhou, R-F. Yang, J. Chen, Y-C. Guo, F. You, X-E. Zhang, *Anal. Chem.* 2006, 78, 997-1004; (e) K. A. Chester, A. Mayer, J. Bhatia, L. Robson, D. I. R. Spencer, S. P. Cooke, A. A. Flynn, S. K. Sharma, G. Boxer, R. B. Pedly, R. H. Begent, *Cancer Chemother. Pharmacol.* (*suppl.*) 2000, S8-S12; (f) P. Ravn, A. Danielczyk, K. B. Jensen, P. Kristensen, P. A. Christensen, M. Larsen, U. Karsten, S. Goletz, *J. Mol. Biol.* 2004, 343, 985-996.
- F. B. E. Power, P. J. Hudson, *J. Immuno. Methods* 2002, 242, 193-204.
- G. J. Atwell, K. A. Breheney, L. J. Lawrence, A. J. McCoy, A. A. Kortt, P. J. Hudson, *Protein Eng.* 1999, 12, 597-604.
- H. (a) H. Yamaguchi, A. Harada, *Top. Curr. Chem.* 2003, 228, 237-258; (b) I. Tomlinson, P. Holliger, *Methods Enzymol.* 2000, 326, 461-479.
- I. (a) P. Carter, R. F. Kelley, M. L. Rodrigues, B. Snedecor, M. Covarrubias, M. D. Velligan, W. L. T. Wong, A. M. Rowland, C. E. Kotts, M. E. Carver, M. Yang, J. H. Bourell, M. H. Shepard, D. Henner, *Bio/Technology* 1992, 10, 163-172; (b) A. J. Cumber, E. S. Ward, G. Winter, G. D. Parnell, E. J. Wawrzynczak, *J. Immunol.* 1992, 149, 120-126; (c) A. Natarajan, C-Y. Xiong, H. Albrecht, G. L. DeNardo, S. J. DeNardo, *Bioconjugate Chem.* 2005, 16, 113-121; (d) J. Casey, D. J. King, L. C. Chaplin, A. M. R. Haines, R. B. Pedly, A. Mountain, G. T. Yarranton, R. H. J. Begent, *Br. J. Cancer* 1996, 74, 1397-1401; (e) D. J. King, A. Turner, A. P. Farnsworth, J. R. Adair, R. J. Owens, R. B. Pedly, D. Baldock, K. A. Proudfoot, A. D. Lawson, N. R. Beeley, *Cancer Res.* 1994, 54, 6176-6185.
- J. M. D. Winthrop, S. J. DeNardo, H. Albrecht, G. R. Mirick, L. A. Kroger, K. R. Lamborn, C. Venclovas, M. E. Colvin, P. A. Burke, G. L. DeNardo, *Clinical Cancer Res.* (*suppl.*) 2003, 9, 3845s-3853s.
- K. Q. Wang, T. R. Chan, R. Hilgraf, V. V. Fokin, K. B. Sharpless, M. G. Finn, *J. Am. Chem. Soc.* 2003, 125, 3192-3193.
- L. N. J. Agard, J. A. Prescher, C. R. Bertozzi, *J. Am. Chem. Soc.* 2004, 126, 15046-15047.
- M. A. E. Speers, G. C. Adam, B. F. Cravatt, *J. Am. Chem. Soc.* 2003, 125, 4686-4687.
- N. T. S. Seo, Z. Li, H. Ruparel, J. Ju, *J. Org. Chem.* 2003, 68, 609-612.
- O. F. Fazio, M. C. Bryan, O. Blixt, J. C. Paulson, C-H. Wong, *J. Am. Chem. Soc.* 2002, 124, 14397-14402.
- P. S. S. Gupta, J. Kuzelka, P. Singh, W. G. Lewis, M. Manchester, M. G. Finn, *Bioconjugate Chem.* 2005, 16, 1572-1579.
- Q. A. J. Link, D. A. Tirrell, *J. Am. Chem. Soc.*, 2003, 125, 11164-11165.

BRIEF SUMMARY OF THE INVENTION

In one aspect, the present invention provides for a method of covalently attaching two proteins to form a conjugate protein, said method comprising contacting a first protein component having from one to eight attached alkyne moieties with a second protein component having an attached linking group with a terminal azide moiety under conditions sufficient for 1,2,3-triazole formation to occur and produce said conjugate protein.

In another aspect, the present invention provides for a method of preparing a multivalent scFv, said method comprising: (a) contacting a first scFv component having from one to eight attached alkyne moieties with a second scFv component having an attached linking group with a terminal azide moiety under conditions sufficient for 1,2,3-triazole formation to occur; and optionally (b) attaching additional scFv components to the product of step (a) in a sequential manner by contacting the product of each step with another scFv component having an attached linking group with a terminal azide moiety under conditions sufficient for 1,2,3-triazole formation; to produce said multivalent scFv.

In one particular aspect, the present invention provides for a method of making a di scFv which targets the MUC-1 mucin that is expressed on epithelial cancer cells.

In yet another aspect, the present invention provides for conjugate protein compositions (e.g., multivalent scFv compositions) comprising a plurality of proteins components (e.g., single chain antibody fragments) cross-linked through at least one linking group comprising at least one 1,2,3-triazole moiety, wherein at least 50 percent of the protein components in the conjugate protein has only one site available for cross-linking.

BRIEF DESCRIPTION OF THE DRAWINGS

FIG. 7 illustrates the ELISA results of the binding of monovalent scFv and the corresponding divalent scFv (i.e., di-scFv-14) to synthetic MUC-1 peptide and DU145 cells. Error bars represent the standard deviation from triplicate experiments.

DETAILED DESCRIPTION OF THE INVENTION

Definitions and Abbreviations

Figure 1:
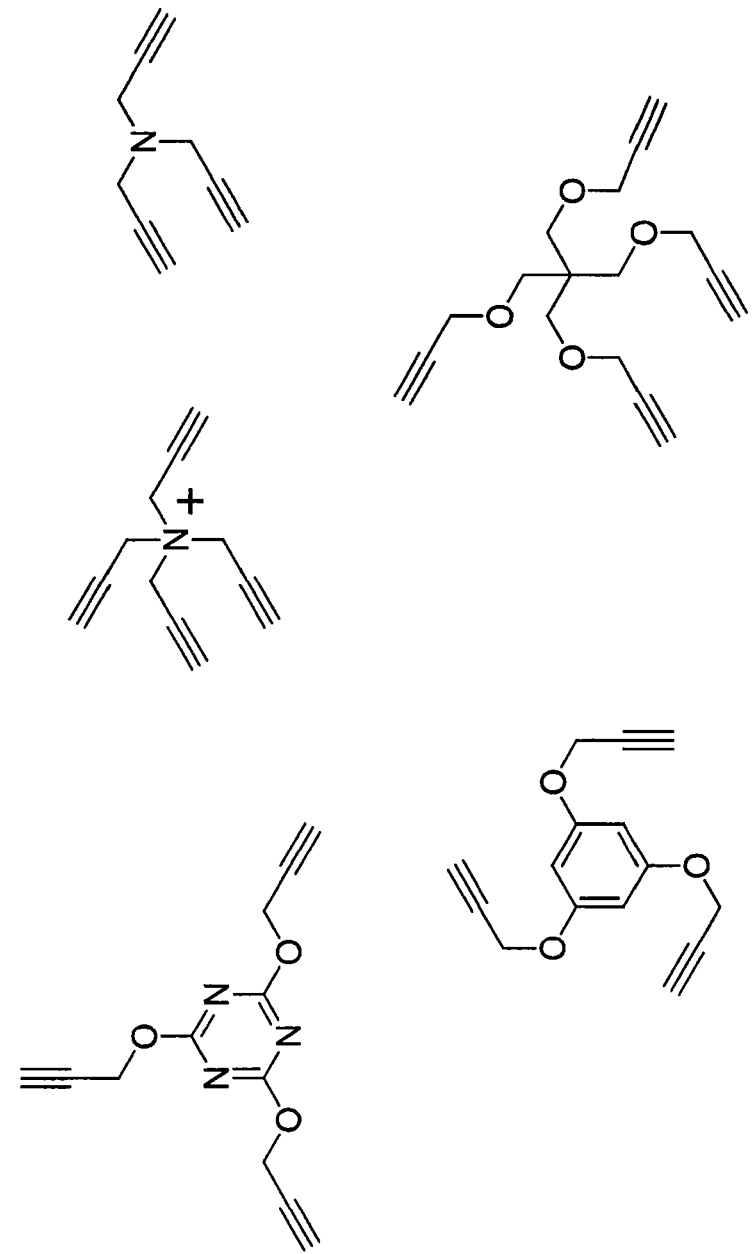
FIG. 1 illustrates compounds having a plurality of alkynyl moieties useful in the conjugation reactions described herein.

As used herein, the term "macromolecule" refers typically to a large biomolecule, such as, for example, protein, polypeptide, polynucleotide, DNA, RNA, and the like.

As used herein, the term "conjugate protein" or "conjugated protein" refers to a compound having two or more individual proteins components that are cross-linked to each other. The protein components in the present invention are preferably those having a protein of a molecular weight of at least 5 kDa.

As used herein, the abbreviation scFv stands for single chain variable fragment which is a antibody fragment, that is a fusion of the variable regions of the heavy and light chains of the antibody, typically linked together with a polypeptide linker.

The Method

In one aspect, the present invention provides for a novel chemical method to connect two macromolecules (e.g., proteins such as an antibody fragment) to each other using an alkyne-azide 1,3-dipolar cycloaddition cross-linking reaction. In the inventive method, the first macromolecule comprises at least one reactive functional group, i.e., an azide or and alkyne, attached thereto; and the second macromolecule has attached thereto a single linking group comprising a reactive functional group (i.e., an azide or alkyne) that is complementary to the reactive group found on the first macromolecule.

Surprisingly, the inventors have discovered that when at least one of the macromolecule coupling partners comprises a linker which displays a plurality (i.e., more than one) of functional groups required for the 1,3-dipolar cyclization reaction (e.g., an azide or alkyne), the 1,3-dipolar cycloaddition reaction with the other macromolecule proceeds efficiently to produce a 1,2,3-triazole moiety and to result in cross-linking of the two macromolecules in excellent yield. Without being bound by any particular theory, it is thought that the increase in the effective concentration of at least one of the reactive functional group required for the 1,3-dipolar cycloaddition reaction in the reaction medium is responsible for the enhanced rate of formation of the conjugated macromolecule product.

In view of the above, in one embodiment, the present invention provides for a method of covalently attaching two proteins to form a conjugate protein, said method comprising contacting a first protein component having from one to eight attached alkyne moieties with a second protein component having an attached linking group with a terminal azide moiety under conditions sufficient for 1,2,3-triazole formation to occur and produce said conjugate protein.

An embodiment of the inventive method is illustrated in Scheme 1 (below).

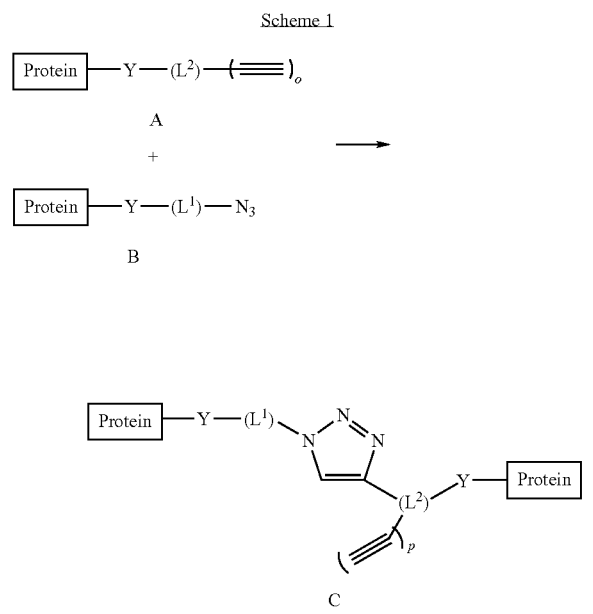

As shown in Scheme 1, a protein A comprising, at least one, but preferably a plurality of alkynyl groups will efficiently undergo a 1,3-dipolar cycloaddition reaction with a second protein B comprising an azido group to produce a conjugated protein product C having a 1,2,3-triazole moiety. Typically the 1,2,3-triazole moiety formed in the reaction will have a 1,4-substitution pattern (as represented by the triazole moiety in Scheme 1), although 1,5-substitution is also possible. In Scheme 1, $L^1$ and $L^2$ each represent a linking group; Y represents a connector group; the subscript o is an integer from 1 to 8, preferably from 2 to 8; and the subscript p is an integer from 0 to 7, preferably from 1 to 7. The linking groups, $L^1$ and $L^2$, are preferably hydrophilic groups. In one embodiment, the linking group comprises a polyoxyalkylene glycol, polypeptide, or other biopolymer derivative; more preferably a polyethylene glycol or a co-block polyethylene-polypropylene glycol derivative. In a preferred embodiment, the linking group comprises a polyethylene glycol. Moreover, $L^1$ and $L^2$ in A and B are independently selected, and thus may not be the same. The symbol Y represent a connector group, typically a functional group that connects the linking group to the protein molecule. Suitable connector groups include, but are not limited to, —C(O)$C_{1-3}$ alkylene-, succinimidyl, triazinyl, —C(O)—, —C=N—, —NHC(O)CH$_2$CH$_2$—, —OC(O)CH$_2$CH$_2$—, —S(O)$_2$CH$_2$CH$_2$—, —NHC(O)—, —NHC(S)—, —O—, —N(H)—, —C(O)NH—, —C(O)O—. In one embodiment, Y is —C(O)$C_{1-3}$ alkylene- or succinimidyl. In another embodiment, Y is —C(O)$C_{1-3}$ alkylene-. In yet another embodiment, Y is succinimidyl.

Moreover, when a protein component A comprising a plurality of alkynyl moieties (i.e., the subscript o is from 2-8) is conjugated with B, the conjugate protein product C can have additional alkynyl group(s) remaining. Any remaining alkynyl groups in the conjugate protein C can be further derivatized to attach another molecule of interest, such as, a peptide, a protein, an antibody, an antibody fragment, a reporter molecule (e.g. a fluorescent group such as rhodamine or quantum dots) and a chelating agent (e.g., 1,4,7,10-Tetraazacyclododecane-1,4,7,10-tetraacetic acid (DOTA)).

In one embodiment, the first protein component has from one to three attached alkyne moieties. In another embodiment, the first protein component has from three to six alkyne moieties. In one aspect of this embodiment, the first protein component has the formula:

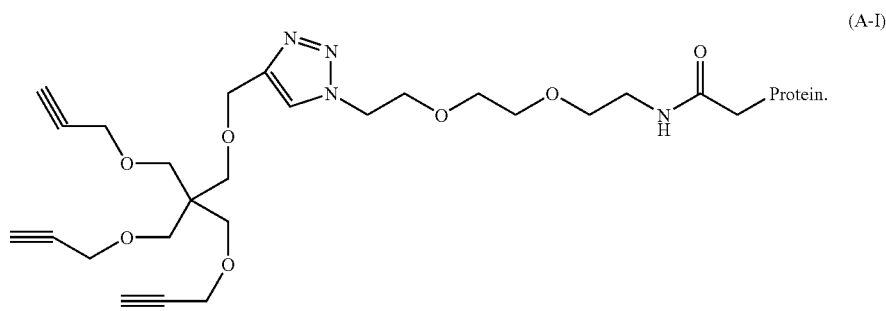

(A-I)

In another embodiment, in the inventive method the second protein component has the formula:

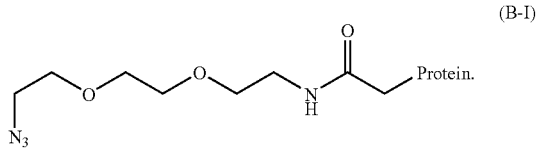

(B-I)

In yet another embodiment, the conjugate protein has the formula:

(C-I)

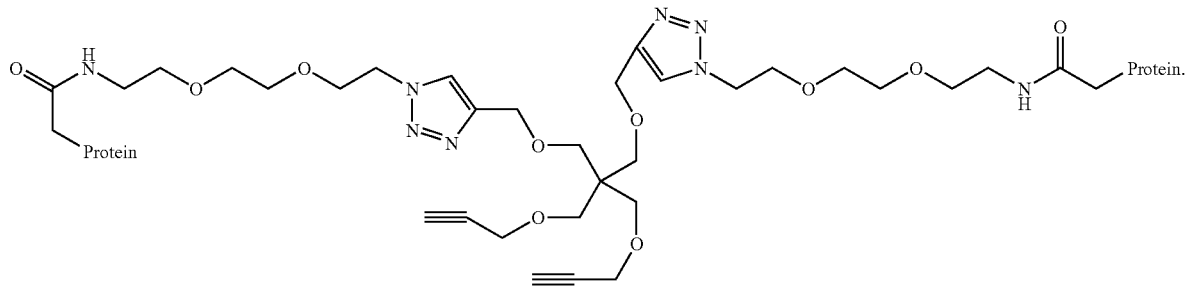

In one preferred embodiment, the present invention provides a method of preparing a multivalent scFv, the method comprising:

(a) contacting a first scFv component having from one to eight attached alkyne moieties with a second scFv component having an attached linking group with a terminal azide moiety under conditions sufficient for 1,2,3-triazole formation to occur; and optionally (b) attaching additional scFv components to the product of step (a) in a sequential manner by contacting the product of each step with another scFv component having an attached linking group with a terminal azide moiety under conditions sufficient for 1,2,3-triazole formation; to produce a multivalent scFv.

In the methods above, the single chain variable antibody fragment in the first scFv and second scFv component can be a construct that targets the tumor-associated MUC-1 mucin antigen. MUC-1 mucin is a peptide that is expressed in epithelial cancer cells, such as in breast cancer or prostate cancer cells, and is a unique target for cancer therapies. In a preferred embodiment, the recombinantly engineered scFv construct that targets MUC-1 contains only one cysteine group to which a linking group comprising the alkyne or azido moiety can be attached, to result in site-specific conjugation of the linking group to the scFv construct.

Method step (a) of this embodiment is illustrated in Scheme 1 (see above) when the protein is a scFv. Moreover as set forth in method step (b), when the protein component A (e.g., a scFv) has a plurality of alkynyl groups, the valency of a scFv compound prepared in step (a) of the method can be further increased by repeating the process described in step (a) in an iterative fashion each time using the multivalent scFv (e.g., divalent scFv) prepared in the previous iteration as a "first scFv component" and reacting it with another second scFv component having an attached a linking group with a terminal azide moiety to form multivalent scFv with increased valency (e.g., trivalent scFv).

In one embodiment of the method, the first scFv component has from one to four alkyne moieties present in a linking group. In another embodiment, the first scFv component has from two to eight alkyne moietys in a linking group, more preferably between three and six alkyne moieties, and more preferably three alkyne moieties. In one aspect of this embodiment, the linking group is attached to a scFv moiety through a thio ether linkage to a cysteine residue present on a scFv moiety.

In yet another embodiment the first scFv component has the formula:

(A-II)

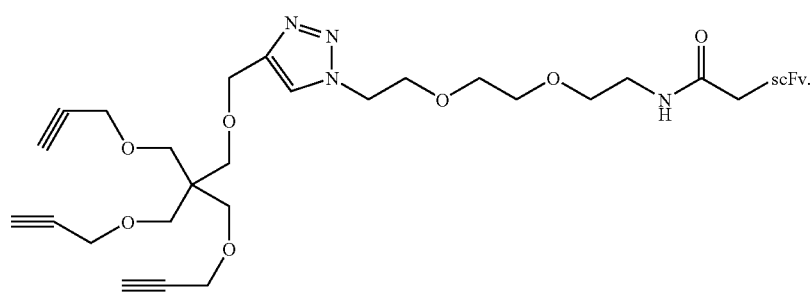

In yet another embodiment, in the method, the second scFv component having an attached linking group with a terminal azide moiety has the formula:

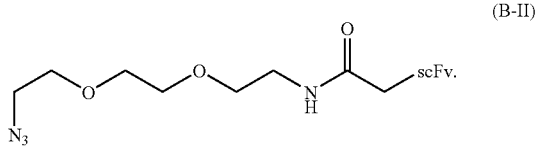

(B-II)

In one embodiment of the invention, the multivalent scFv prepared by the inventive method is a di-scFv, or in another embodiment the multivalent scFv is a tri-scFv, or in yet another embodiment the multivalent scFv is a tetra-scFv. In one preferred aspect, the multivalent scFv prepared by the inventive method is a covalent di scFv of the formula:

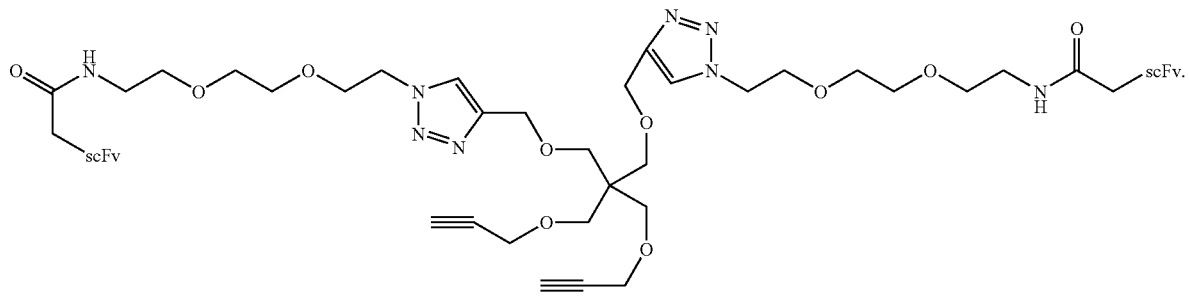

(C-II)

In a preferred embodiment the scFv moiety in compounds A-II, B-II and C-II is the single chain variable antibody fragment that targets the tumor-associated MUC-1 antigen.

The molar ratio of a first scFv component (or protein) comprising alkynyl moieties to a second scFv component (or protein) comprising an azido moiety in the inventive method is typically in the range from about 10:1 to about 1:2, more preferably between about 5:1 to about 1:2, and even more preferably between about 3:1 to about 1:1.

The method of the invention to form a conjugated protein (e.g., a multivalent scFv) utilizes Huisgen's 1,3-dipolar cycloaddition reaction to form a 1,2,3-triazole moiety in a cross-linked protein product. The noted 1,3-dipolar cycloaddition reaction is compatible with a number of other functional groups typically found in biological molecules and in biological systems; and is relatively insensitive to oxygen or water (see, Sharpless, K. B., *Drug Discovery Today*, 8:24, 2003, 1128.). The present method which utilizes a 1,3-dipolar cycloaddition reaction can be performed under a wide range of conditions, and the conditions described herein should not be construed as limiting.

For example, the dipolar cycloaddition reaction disclosed in the inventive method may be accelerated in the presence of a metal catalyst. In one embodiment, the method does not use a catalyst. In a preferred embodiment, a metal catalyst is added.

Metal catalysts that are useful in the present invention are metal salts comprising metal ions selected from the group including Cu, Au, Ag, Hg, Cd, Zr, Ru, Fe, Co, Pt, Pd, Ni, Rh and W, among others. Preferably, the metal salt comprises a copper I or copper II metal ion. For copper-based catalysts, copper I is believed to be the active catalytic species. Suitable copper I salts for use in the inventive method include, for example, Cu(I)I, Cu(I)Cl, Cu(I)Br, Cu(I)O, Cu(OTf)$C_6H_6$, [Cu($CH_3CN$)$_4$]$PF_6$. In a preferred embodiment, the active copper I catalyst is formed in situ from the combination of a copper II metal species and a reducing agent. Suitable copper II metal salts include Cu(II)$SO_4$, Cu(II)$Cl_2$ Cu(II)($NO_3$)$_2$, Cu(II)$Br_2$, Cu(II)($ClO_4$)$_2$, Cu(II)O and Cu(II)Acetate, and derivatives thereof. In one preferred embodiment, the copper II salt is Cu(II)$SO_4$. Preferred reducing agents include, ascorbate, metallic copper, quinone, hydroquinone, vitamin $K_1$, glutathione, cysteine, $Fe^{2+}$. $CO^{2+}$ and applied electric potential. Further preferred reducing agents include metals selected from the group consisting of Al, Be, Co, Cr, Fe, Mg, Mn, Ni, and Zn.

Additionally, in some embodiments, ligand can be added to coordinate to, and stabilize the active copper species. Ligands that can function in this capacity and are useful for the inventive method are selected from the group consisting of nitrile, amine, phosphite, phosphine, isonitrile, a nitrogen containing heterocycle, carboxylate, halide, alcohol, thiol and sulifide, among others. In certain embodiments, the ligand is selected from the group consisting of 2,6-lutidine, triethyl amine, diisopropylethylamine, pyridine, triphenylphosphine, triethylphosphite, bathphenanthroline (see, Finn. M. G., *Bioconjugate Chem.* 2005, 16, 1572), tris(2-carboxyethyl)phosphine hydrochloride and tris[(1-benzyl-1H-1,2,3-triazol-4-yl)methyl]amine (TBTA). In a preferred embodiment, the ligand is TBTA.

The cycloaddition reaction to form a multivalent scFv or another conjugate protein can proceed at a number of temperatures, for example, from about −78° C. to about 50° C. In one embodiment, the cyclization reaction proceeds at a temperature from about −30° C. and about 35° C. In one preferred embodiment, the cyclization reaction is carried out at about room temperature (25° C.).

Additionally, the cycloaddition reactions disclosed for the inventive methods are generally carried out in the presence of at least one solvent, and in some embodiments, in a combination of two or more solvents. An inert solvent is preferred, particularly one in which the reaction ingredients are substantially soluble and stable, although complete solubility is not required. Suitable solvents are typically water-based solvents, such as for example, aqueous buffers. In one embodiment, the solvent is a biological buffer system, including, but not limited to Phosphate Buffered Saline (PBS), MES, Bis-Tris, PIPES (no salt), ACES, MOPS, TES, HEPES (no salt), HEPPS, Tricine, Bicine, CHES, CAPS MOPSO, DIPSO, HEPPSO, POPSO, AMPSO and CAPSO, Tris acetate-EDTA, Tris-borate-EDTA, Tris-Glycine, Tris-Tricine, Tris-Glycine-SDS, Tris-Tricine-SDS, Tris, Sodium Chloride-Sodium Citrate, PIPES, Cacolydate, Cholamine chloride, Acetamidoglycine, Glycinamide, BES and EDTA buffers, and the like (see, for example, Ferguson W. J., et al., *Anal. Biochem.* 104: 300 (1980); Good, N. E., (1966) *Biochemistry*, 5, 467-477). In another preferred embodiment, the solvent is an aqueous buffer that maintains the pH of the reaction solution between about 5 to about 9; more preferably between about 6 and about 8; and even more preferably between about 6 and 7. In another preferred embodiment, the solvent is an aqueous biological buffer selected from the group consisting of PBS, MES, ADA, PIPES, ACES, Cholamine chloride, BES, TES, HEPES (no salt), Acetamidoglycine, Tricine, Glycinamide and Bicine. In a specific embodiment, the aqueous buffer is preferably PBS. In another embodiment, the aqueous solvent is water.

Alternatively, it may be desirable to carry out the cycloaddition reaction in inert organic solvents such as ethers (e.g., diethyl ether, 1,2-dimethoxyethane, tetrahydrofuran); halogenated solvents (e.g., chloroform, dichloromethane, dichloroethane); aliphatic or aromatic hydrocarbon solvents (e.g., benzene, xylene); esters and ketones (e.g., ethyl acetate); and polar aprotic solvents (e.g., acetonitrile, dimethylsulfoxide, dimethylformamide).

In some embodiments, cycloaddition reaction can be run in a biphasic mixture of solvents (i.e., a combination of organic and aqueous solvents), in an emulsion or suspension. In certain embodiments, the cycloaddition reaction can be run in the solid phase with one of the reactants, e.g., a first or second protein component, tethered or anchored to a solid support.

The manner or order of addition of the reaction ingredients and solvent are also not generally critical to the success of the reaction, and may be accomplished in any conventional fashion. The reaction steps may be effected by the incremental addition of one of the starting materials to the other.

Preparation of Alkynyl- and Azido-Protein Precursor Compounds

The protein precursors, A and B, comprising alkynyl or azido moieties, which are useful for the inventive method, can be prepared by known synthetic methods. Typically, the alkynyl- or azido-protein precursors are made by first preparing a linking group comprising the azido or alkynyl moieties, followed by tethering the linking group to a protein. Alternatively, it is also possible to synthesize the alkynyl- or azido-protein precursors by preparing a protein comprising a linking group and subsequently modifying the linking group to introduce the azido or alkynyl moiety.

Synthesis of Alkynyl-Protein Precursors

For example, alkynyl-protein precursors having a linker comprising polyethylene glycol can be prepared by the synthetic route shown in Scheme 2. In Scheme 2, X represents a leaving group, the subscript n is an integer from 1 to 10, and hal represents a halogen atom. In polyethylene glycol compound i, the leaving group, X, is displaced by an azide to form an azido compound. In the second step, the free hydroxy group on the azido compound is further alkylated with an alkynyl moiety, such as propargyl bromide, under basic conditions to produce the alkynyl compound ii. The azido group in ii is reduced to an amino group using a reducing agent, such as triphenylphosphine, to produce amino-alkyne iii. The amino-alkyne compound iii can be further reacted with an electrophile that contains an additional reactive functional group which can further react with complementary reactive functional group on a protein. Examples of suitable electrophiles include, haloacetyl halide or maleimide, which will react with iii to form a compounds, iv and v, respectively. Compounds iv and v can be conjugated directly to a nucleophilic (Nu) functional group present on a protein, such as an amino or thiol group to produce a protein precursor (e.g. vi, vii) comprising an alkynyl moiety.

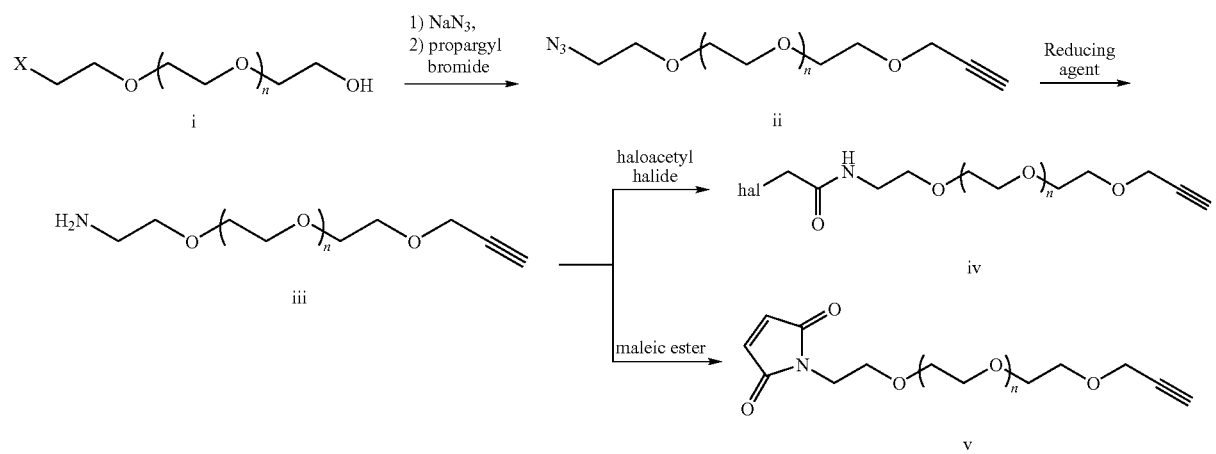

Scheme 2

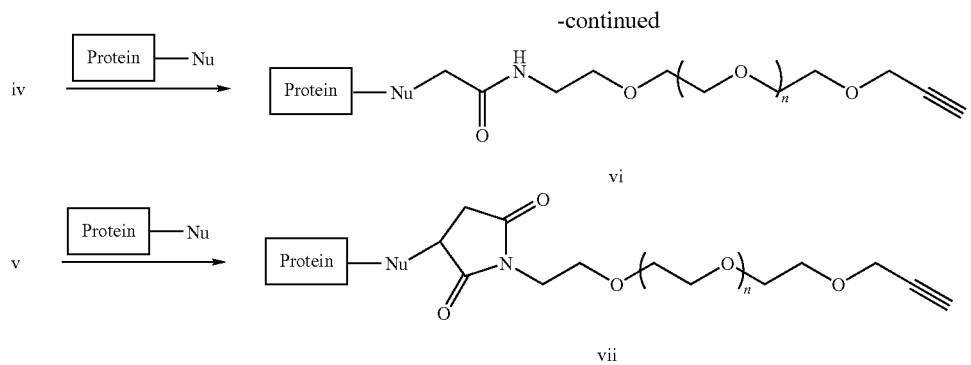

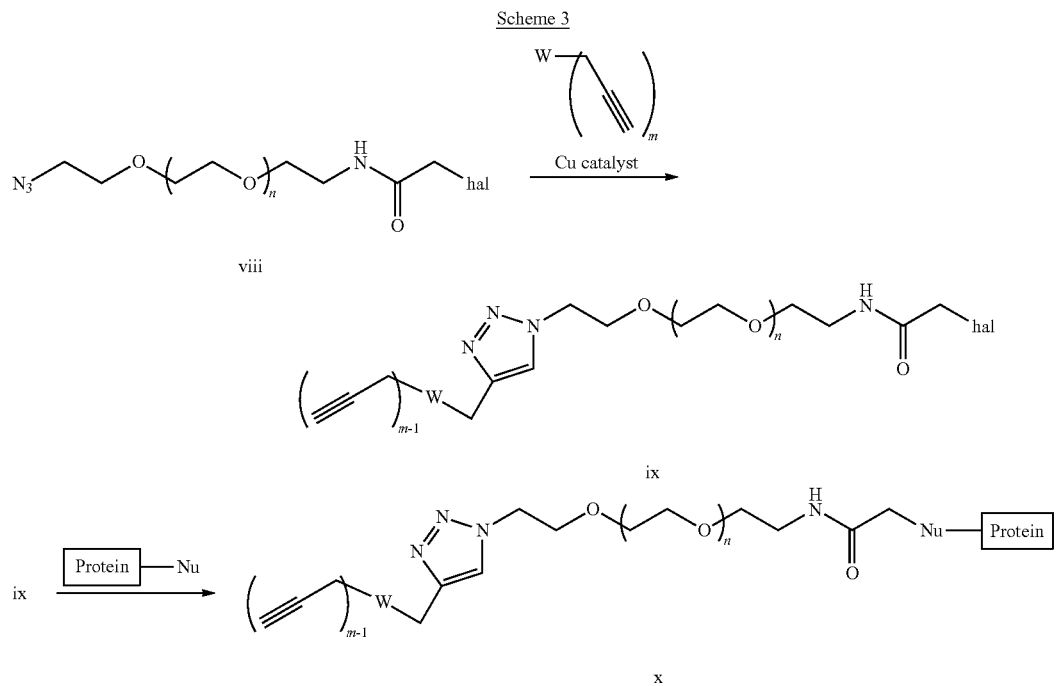

In another example, a protein precursor compound comprising a plurality of alkynyl groups can be prepared according to the synthetic procedure outlined in Scheme 3. As shown in Scheme 3, a compound having the formula W-$(CH_2-C{\equiv}CH)_m$, in which W represents an organic molecule core to which multiple alkynyl groups are attached, can react with an azido group present on a polyethylene glycol linker viii to form compound ix that has a plurality of alkynyl groups. Compound ix can be conjugated directly to a nucleophilic (Nu) functional group present on a protein, such as an amino or thiol group, to produce a protein precursor (e.g. x) comprising at least one alkynyl moiety. In Scheme 3, m is an integer from 2 to 5 and the subscript n is an integer from 1 to 10, and hal is a halogen. Examples of compounds of the formula W-$(CH_2-C{\equiv}CH)_m$ are set forth FIG. 1. Additional examples of compounds of formula W-$(CH_2-C{\equiv}CH)_m$ use-ful for the invention are described in Wu A. M. *Cancer Biother Radiopharm.* 2001 April; 16(2):103-8; Kwasnikowski P. et al. *J Immunol Methods.* 2005 Dec. 20; 307(1-2): 135-43; Hudson P. J. et al. *J Immunol Methods.* 1999 Dec. 10; 231(1-2): 177-89; and Atwell J. L. et al. *Protein Eng.* 1999 July; 12(7):597-604; all of which are incorporated herein by reference in its entirety.

Synthesis of Azido-Protein Precursors

Similarly, protein precursors comprising an azido group can be prepared as shown in Scheme 4. In Scheme 4, hal is halogen, the subscript n is an integer from 1 to 10. As shown in Scheme 4, polyethylene glycol compound xi is reacted with an electrophile that contains an additional reactive functional group which can further react with complementary reactive functional group on a protein. Examples of suitable electrophiles include, haloacetyl halide or maleimide, which will react with xi to form a compounds, xii and xiii, respectively. Compounds xii and xiii can be conjugated directly to a nucleophilic (Nu) functional group present on a protein, such as an amino or thiol group to produce a protein precursor (e.g. xiv, xv) comprising an azido group.

Conjugated Proteins

In another aspect, the present invention provides for a conjugate protein, in which the conjugate protein is comprised of a plurality of protein components cross-linked through at least one linking group comprising at least one

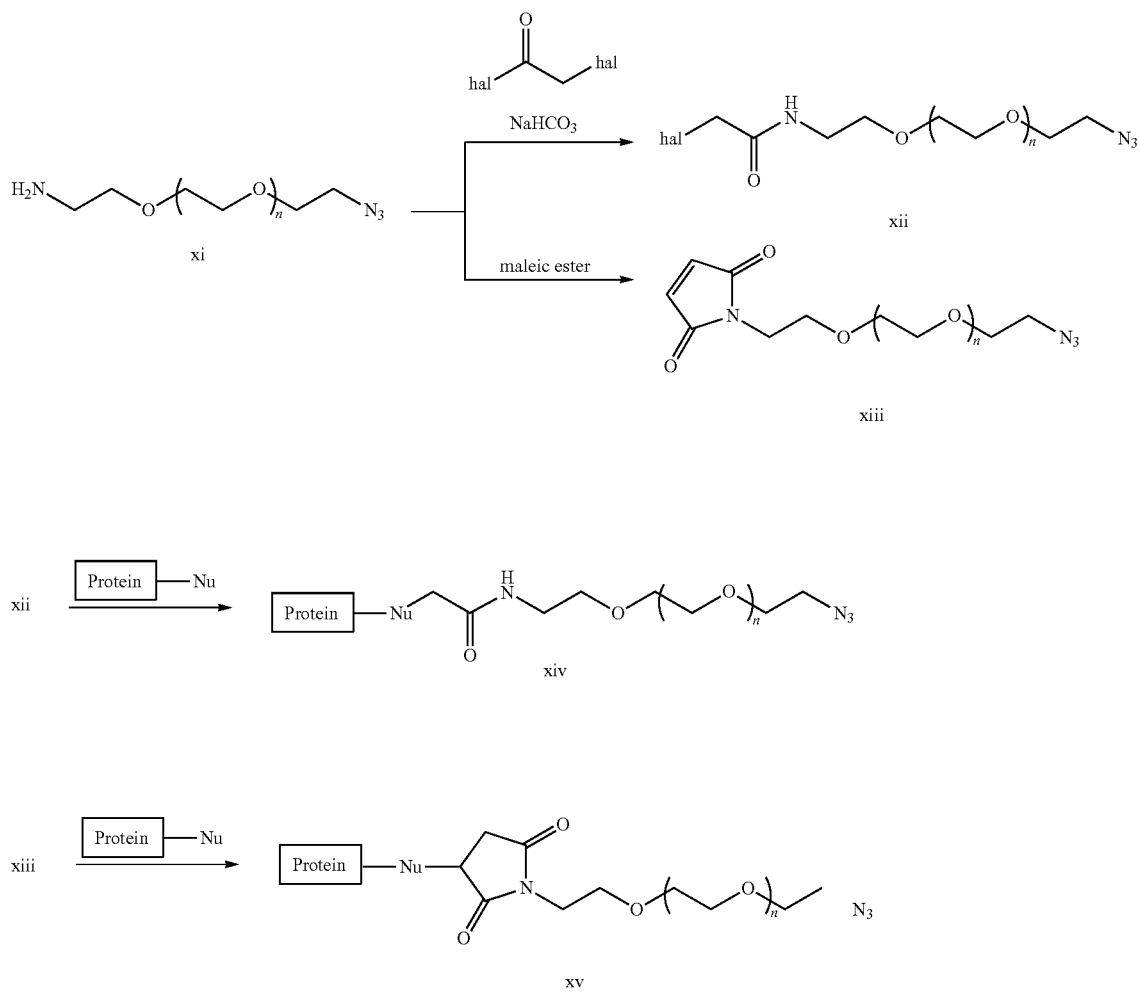

Although the synthetic methods described above illustrate the synthesis of protein precursors comprising alkynyl or azido moietys that are attached through a linking group which comprises a linear polyethylene glycol group, the invention is not limited to linking groups comprising linear polyethylene glycol groups. A skilled artisan would recognize other linking groups that are compatible with biological systems that would be useful for the inventive method. Other preferred linking groups include, for example, those that comprise a branched polyethylene glycol or a co-block polyoxyalkylene glycol.

1,2,3-triazole moiety, wherein at least 50 percent of the protein components in the conjugate protein has only one site available for cross-linking. In certain aspects of this embodiment, at least 60, 70, 80, 90 or 100 percent of the protein components in the conjugate protein has only one site available for cross-linking. In another embodiment, the protein conjugate has the formula C which is illustrated in Scheme 1. In one aspect of this embodiment, the linking groups in formula C comprise a polyethylene glycol group. In yet another aspect of this embodiment, the linking groups in formula C are the same. In yet another aspect of this embodiment, the linking groups in formula C are different. In another embodiment, the conjugate protein is a multivalent scFv. In certain aspects of this embodiment, the multivalent scFv is a di-scFv, or a tri-scFv or a tetra-scFv.

In certain embodiments, the multivalent scFv is a di-scFv having the structure:

with TLC mobility. NMR experiments were conducted on either a Varian 400 MHz or 600 MHz instrument using CDCl₃ (99.9% D) as a solvent. Chemical shifts are relative to the deuterated solvent peak and are in parts per million (ppm). Low resolution mass spectra were acquired using a Thermo-Quest Surveyor™ LC/MS or Qtrap LC/MS instruments (Ap-

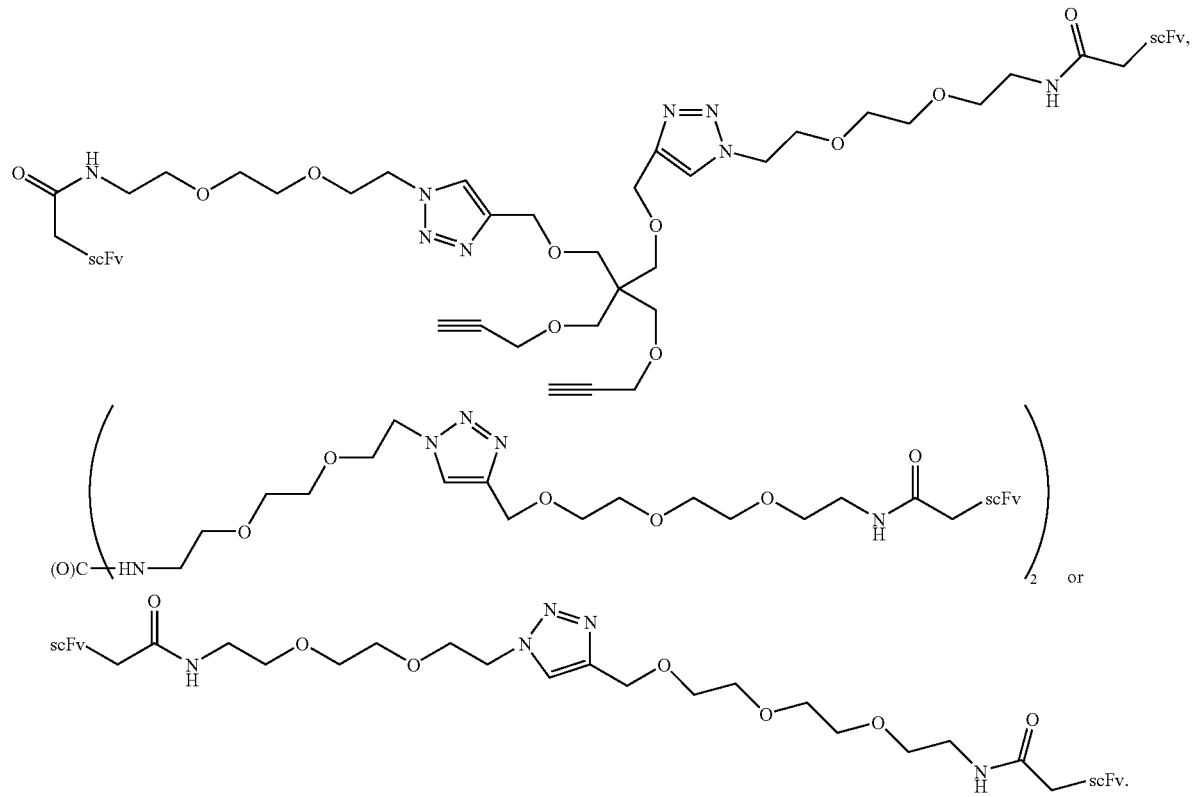

In another embodiment, the scFv in the multivalent scFv is an antibody fragment that binds to the MUC-1 mucin antigen expressed in breast cancer and prostate cancer cells.

The following examples are provides to illustrate certain aspects of the invention and should not be construed to limit the invention in any way.

EXAMPLES

General:

All materials were obtained from commercial sources and used without additional purification. Solvents used in the synthesis were purchased in capped DriSolv™ bottles and used directly without further purification and stored under argon. All glassware utilized was flame-dried before use. Glass-backed TLC plates (Silica Gel 60 with a 254 nm fluorescent indicator) were used without further manipulation and stored over desiccant. Developed TLC plates were visualized under a short-wave UV lamp, stained with an I₂ mixture, and/or by heating plates that were dipped in ammonium molybdate/cerium (IV) sulfate solution. Flash column chromatography (FCC) was performed using flash silica gel (32-63/μm) and employed a solvent polarity which correlated plied Biosystem Inc., Foster City, Calif.). FT-IR spectra were acquired from a Galaxy FTIR 3000 instrument at 25° C.

Example 1

Synthesis of 2-Bromo-N-{2-[2-(2-prop-2-ynyloxy-ethoxy)-ethoxy]-ethyl}-acetamide (5)

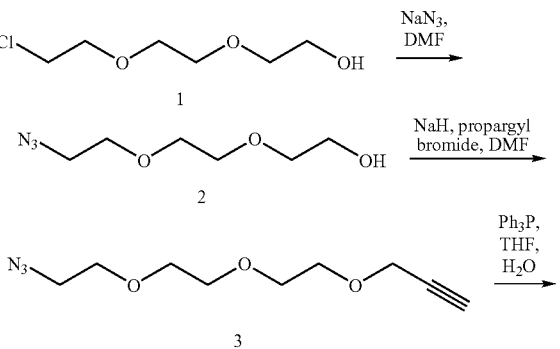

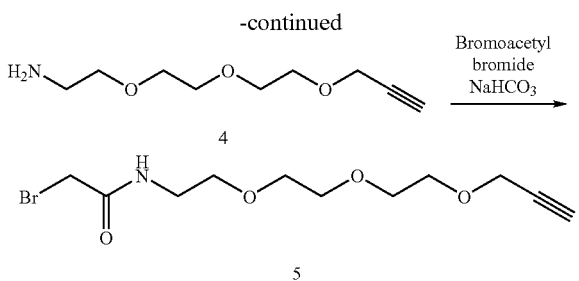

2-[2-(2-azidoethoxy)ethoxy]ethanol (2): In a 250 mL flask, 2-[2-(2-chloroethoxy)ethoxy]ethanol (1) (6000 mg, 35.7 mmol), NaN$_3$ (6964 mg, 107 mmol) and tetrabutylammonium iodide (TBAI) (656 mg, 1.7 mmol) were added to 80 mL DMF. The temperature was slowly raised to 120° C. and the reaction mixture was stirred under argon overnight. The solvent was evaporated and the residue was purified by FCC to afford 2 as slightly yellow oil (4150 mg, 66%). $^1$H NMR (400 MHz, CDCl$_3$): δ 3.29 (t, J=5.2 Hz, 2H), 3.50 (m, 2H), 3.57-3.64 (m, 8H). $^{13}$C NMR (100 MHz, CDCl$_3$): δ 50.59, 61.60, 69.98, 70.34, 70.59, 72.56.

3-(2-(2-(2-azidoethoxy)ethoxy)ethoxy)prop-1-yne (3): in a 50 mL flask, 2 (350 mg, 2 mmol) was dissolved in 10 mL DMF. NaH (58 mg, 2.4 mmol) and subsequently propargyl bromide (476 mg, 4.0 mmol) were added to the reaction mixture. The reaction mixture was stirred at rt (room temperature) overnight. The solvent was evaporated and the residue was purified by FCC to afford 3 as slightly yellow oil (361 mg, 85%). $^1$H NMR (400 MHz, CDCl$_3$): δ 2.43 (t, J=1.2 Hz, 1H), 3.38 (t, J=5.2 Hz, 2H), 3.66-3.69 (m, 10H), 4.20 (m, 2H). $^{13}$C NMR (100 MHz, CDCl$_3$): δ 50.87, 58.61, 69.31, 70.25, 70.69, 70.87, 70.89, 74.74, 79.83. ESIMS calcd for C$_9$H$_{15}$N$_3$NaO$_3$ [M+Na]$^+$ 236.22, found: 236.28. FTIR (NaCl plate, CH$_2$Cl$_2$): 1118 (C—O str), 2107 (N≡N and C≡C str), 2905 (C—H str).

3-(2-(2-(2-aminoethoxy)ethoxy)ethoxy)prop-1-yne (4): in a 50 mL flask, 3 (150 mg, 0.7 mmol), Ph$_3$P were dissolved in 10 mL THF. The reaction mixture was stirred at rt for 3 hr. To the reaction mixture was added H$_2$O (1 mL) the resultant mixture was stirred for 36 hr at rt. The solvent was evaporated and the residue was purified by FCC to afford 4 as slightly yellow oil (131 mg, quant.). $^1$H NMR (400 MHz, CDCl$_3$): δ 1.46 (br, 2H), 2.35 (t, J=1.6 Hz, 1H), 2.73 (t, J=5.2 Hz, 2H), 3.38 (t, J=5.2 Hz, 2H) 3.50-3.59 (m, 10H), 4.08 (m, 2H). $^{13}$C NMR (100 MHz, CDCl$_3$): δ 41.72, 58.34, 69.04, 70.21, 70.36, 70.54, 73.36, 74.63, 79.60. ESIMS calcd for C$_9$H$_{18}$NO$_3$ [M+H]$^+$ 188.13, found: 188.16. FTIR (NaCl plate, CH$_2$Cl$_2$): 1118 (C—O str), 2111 (C≡C str), 2869 (C—H str), 3249 (N—H str).

2-Bromo-N-{2-[2-(2-prop-2-ynyloxy-ethoxy)-ethoxy]-ethyl}-acetamide (5): To a solution of 4 (50 mg, 0.27 mmol) in CH$_2$Cl$_2$ (3 mL) was added sat. NaHCO$_3$ (3 mL). Under stirring, bromoacetyl bromide (80 mg, 040 mmol) was added. The pH was controlled in the range 8-9 by adding solid NaHCO$_3$. The reaction was stirred at rt for 15 min. CH$_2$Cl$_2$ (5 mL) was added and the reaction mixture was extracted 5×3 mL CH$_2$Cl$_2$. The organic layers were combined, washed with brine, dried with Na$_2$SO$_4$. The solvent was evaporated and the residue was purified by FCC to afford 5 as clear oil (65 mg, 78%). $^1$H NMR (400 MHz, CDCl$_3$): δ 2.42 (t, J=2.4 Hz, 1H), 3.48 (dd, J=5.2, 5.2 Hz, 2H) 3.57 (t, J=5.2 Hz, 2H), 3.62 (m, 4H), 3.66-3.70 (m, 4H), 3.85 (s, 2H), 4.18 (d, J=2.4 Hz, 2H). 6.91 (bs, 1H). $^{13}$C NMR (100 MHz, CDCl$_3$): δ 29.35, 40.11, 58.65, 69.32, 69.56, 70.53, 70.61, 70.76, 74.90, 79.73, 165.86. ESIMS calcd for C$_{11}$H$_{18}$BrNNaO$_4$ [M+Na]$^+$ 330.03, 332.03, found: 330.33, 332.46.

Example 2

Synthesis of N-{2-[2-(2-Azido-ethoxy)-ethoxy]-ethyl}-2-bromo-acetamide (8)

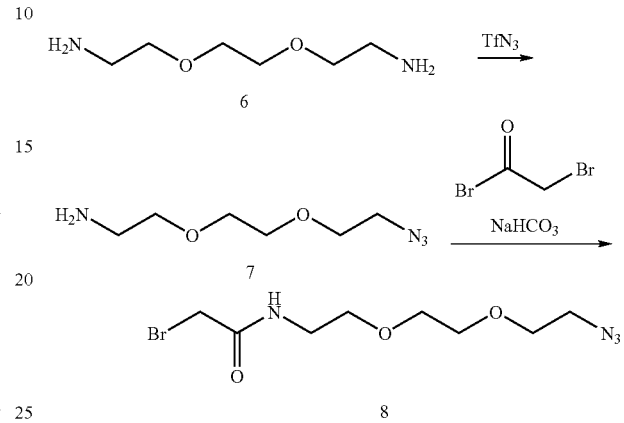

Preparation of Triflic Azide (TfN$_3$): To a solution of NaN$_3$ (3445 mg, 53 mmol) in H$_2$O (12 mL) was added CH$_2$Cl$_2$ (18 mL). The resulting biphasic mixture was cooled in an ice bath and stirred vigorously and treated with Tf$_2$O (3000 mg, 106 mmol) over a period of 60 min. The reaction mixture was stirred in an ice bath for 4 h. The organic phase was separated and the aqueous phase was extracted once with CH$_2$Cl$_2$ (20 mL). The organic extracts were washed with saturated Na$_2$CO$_3$ solution and used without further purification.

2-(2-(2-azidoethoxy)ethoxy)ethanamine (7): 2-(2-(2-aminoethoxy)ethoxy)ethanamine (6) (3137 mg, 21.2 mmol) was dissolved in 10 mL of MeOH and treated with potassium carbonate (1698 mg, 63 mmol) and CuSO$_4$ pentahydrate (14 mg, 0.088 mmol). The TfN3 solution was added dropwise over a period of 8 hr. The reaction was stirred for 18 h and the solvent was removed. Purification of the crude product by flash column chromatography (FCC) provided 7 as slightly yellow oil (1850 mg, 50%). $^1$H NMR (600 MHz, CDCl$_3$): δ 1.86 (s, 2H), 2.88 (t, J=5.4 Hz, 2H), 3.39 (t, J=5.4 Hz, 2H), 3.52 (t, J=5.4 Hz 2H), 3.63-3.68 (m, 6H). $^{13}$C NMR (150 MHz, CDCl$_3$): δ41.88, 50.87, 70.27, 70.51, 70.86, 73.42. ESIMS calcd for C$_6$H$_{15}$N$_4$O$_2$ [M+H]$^+$ 175.21, found: 175.25. FTIR (NaCl plate, CH$_2$Cl$_2$): 1118 (C—O str), 2110 (N≡N str), 2918 (C—H str), 3300 (N—H str).

N-(2-(2-(2-azidoethoxy)ethoxy)ethyl)-2-bromoacetamide (8): To a solution of 7 (32 mg 0.18 mmol) in CH$_2$Cl$_2$ (3 mL) was added sat. NaHCO$_3$ solution (3 mL). The reaction mixture was placed in an ice bath and bromoacetyl bromide (55 mg, 0.27 mmol) was added dropwise. Saturated NaHCO$_3$ solution was added to maintain the pH at about 8. Approximately, 15 min. later, the reaction was stopped by adding 5 mL of CH$_2$Cl$_2$. The organic layer was separated and the aqueous layer was extracted 3×5 mL CH$_2$Cl$_2$. The organic layer was combined, dried with Na$_2$SO$_4$. The solvent was evaporated and the residue was purified by FCC to afford 8 as slightly brown oil (39 mg, 0.13 mmol, 78%). $^1$H NMR (400 MHz, CDCl$_3$): δ 3.35 (t, J=4.8 Hz, 2H), 3.49 (dd, J=10.4, 5.2 Hz, 2H), 3.55 (t, J=4.8 Hz, 2H), 3.60-3.66 (m, 6H), 3.83 (s, 2H), 6.86 (br s, 1H). $^{13}$C NMR (100 MHz, CDCl$_3$): δ 29.27, 40.02, 50.78, 69.53, 70.26, 70.49, 70.69, 165.78. ESIMS calcd for $C_8H_{15}BrN_4NaO_3$ $[M+Na]^+$ 317.02, 319.02, found: 317.38, 319.29. FTIR: 1120.44 (C—O str), 1652.69 (C=O str), 2109.74 (N=N str), 2954.41 (C—H str), 3307.32 (N—H str).

Example 3

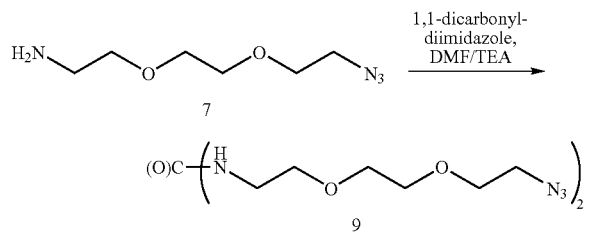

1,3-[bis(2-(2-(2-azidoethoxy)ethoxy)ethyl)]urea (9): 1,1-carbonyldiimidazole (37 mg, 0.22 mmol) and triethyl amine (TEA) (74 mg, 0.57 mmol) were added to 10 mL DMF. Under stirring, compound 7 (100 mg, 0.57 mmol) was added. The reaction mixture was stirred at rt overnight. The solvent was evaporated and the residue was purified by FCC to afford 9 as slightly yellow oil (81 mg, quant.). $^1$H NMR (400 MHz, CDCl$_3$): δ 3.33 (t, J=5.2 Hz, 4H), 3.38 (t, J=5.2 Hz, 4H), 3.5 (t, J=5.2 Hz, 4H), 3.60-3.66 (m, 16H), 7.01 (bs, 2H). $^{13}$C NMR (100 MHz, CDCl$_3$): δ 40.47, 50.86, 70.10, 70.17, 70.35, 70.61, 70.67, 70.77, 159.28. ESIMS calcd for $C_{13}H_{26}N_8NaO_5$ $[M+Na]^+$ 397.39, found: 397.67.

Example 4

Synthesis of Trialkyne Linker 13

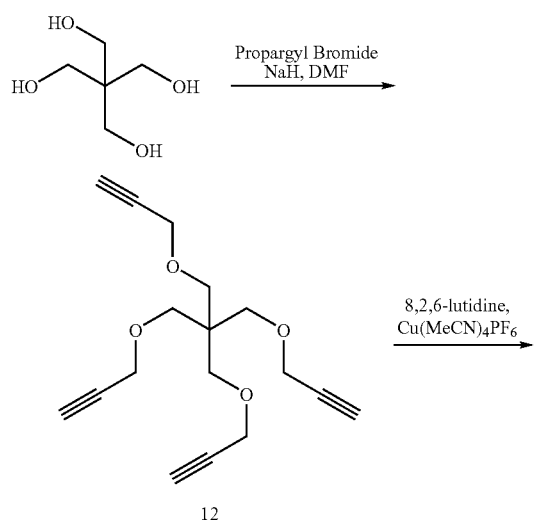

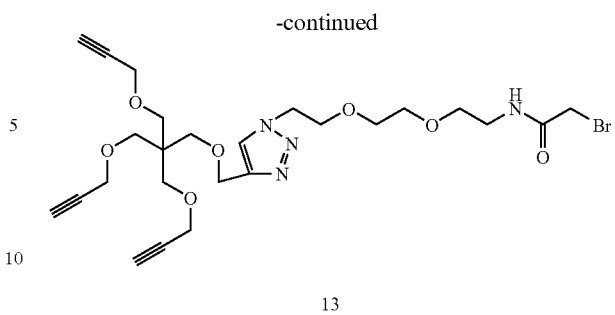

Tetra-alkyne 12: Pentaerythritol (272 mg, 2 mmol) was dissolved at 20 mL DMF, NaH (288 mg, 12 mmol) and propargyl bromide (1420 mg, 12 mmol) was added to the solution. The reaction was stirred at 80° C. overnight. The solvent was removed and the residue was purified by FCC to afford 12 as slightly yellow oil (434 mg, 1.50 mmol, 75%). $^1$H NMR (400 MHz, CDCl$_3$): δ 2.39 (s, 4H), 3.45 (s, 8H), 4.05 (s, 8H). $^{13}$C NMR (100 MHz, CDCl$_3$): δ 44.86, 58.79, 69.06, 74.45, 80.15. ESIMS calcd for $C_{17}H_{20}NaO_4$ $[M+Na]^+$ 311.33, found: 311.22.

Trialkyne Linker 13: The azide linker 8 (30 mg, 0.11 mmol) and tetra-alkyne 12 (62 mg, 0.22 mmol) were dissolved at 3 mL acetonitrile, 2,6-lutidine and Cu(MeCN)$_4$PF$_6$ (8 mg, 0.022 mmol) were added. The reaction was stirred under argon overnight. The solvent was evaporated and the residue was purified by FCC to afford 13 as slightly yellow oil (45 mg, 40%). $^1$H NMR (400 MHz, CDCl$_3$): δ 2.43 (m, 3H), 3.47-3.60 (m, 18H), 3.91 (m, 4H), 4.11 (m, 6H), 4.55 (t, J=5.4 Hz, 2H), 4.64 (s, 2H), 6.93 (bs, 1H), 7.70 (s, 1H). $^{13}$C NMR (100 MHz, CDCl$_3$): δ 29.46, 40.15, 45.17, 50.51, 58.95, 65.46, 69.22, 69.47, 69.65, 69.69, 70.58, 70.72, 74.47, 80.31, 123.69, 145.84, 169.92. ESIMS calcd for $C_{26}H_{37}BrN_4NaO_6$ $[M+2H+Na]^+$ 605.20, 607.19 found: 605.46, 607.44.

Example 5

Synthesis of Rhodamine Azide 15

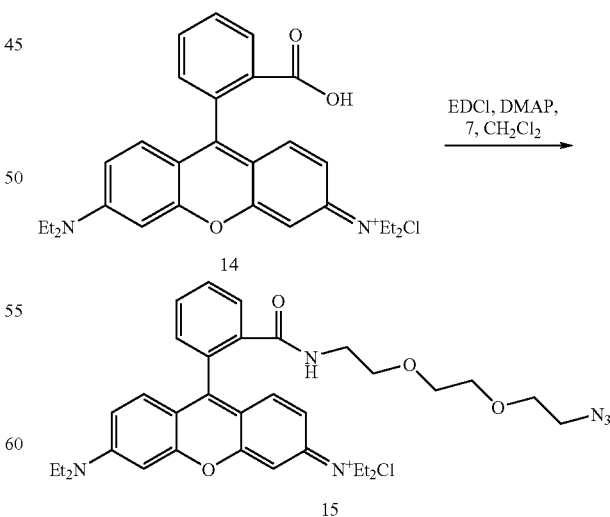

Rhodamine-Azide 15: Rhodamine B (14) (409 mg, 0.85 mmol) and compound 7 (100 mg, 0.57 mmol) were dissolved in 10 mL CH$_2$Cl$_2$, and under stirring, DIPEA (0.3 mL), -Ethyl-3-(3'-dimethylaminopropyl)carbodiimide hydrochloride (EDCI) (326 mg, 1.17 mmol) and DMAP (cat.) were added. The reaction mixture was stirred at rt overnight. The solvent was evaporated and the residue was purified by FCC to afford 15 as bright pink oil (345 mg, 94%). $^1$H NMR (400 MHz, CDCl$_3$): δ 1.15 (t, J=6.8 Hz, 2H), 3.17 (t, J=7.2 Hz, 12H), 3.26-3.37 (m, 14H), 3.47 (dd, J=5.6, 3.6 Hz, 2H), 3.56 (dd, J=5.6, 5.2 Hz, 2H), 6.23 (d, J=2.4 Hz, 1H), 6.25 (d, J=2.4 Hz, 1H), 6.35 (d, J=2.8 Hz, 2H), 6.40 (d, J=8.8 Hz, 2H), 7.03 (m, 1H), 7.39 (m, 2H), 7.86 (m, 1H). $^{13}$C NMR (125 MHz, CDCl$_3$): δ 12.69, 39.34, 44.44, 50.71, 64.89, 67.96, 70.04, 70.08, 70.51, 97.82, 105.59, 108.12, 122.78, 123.86, 128.04, 128.93, 131.06, 132.46, 148.81, 153.33, 153.85, 168.30. ESIMS calcd for $C_{34}H_{42}N_6NaO_4$ [M+Na—HCl]$^+$ 621.73, found: 621.72. FTIR (NaCl plate, CH$_2$Cl$_2$): 1098 (C—O str), 1660 (C=O str), 2113 (N≡N str), 2909 (C—H str), 3310 (N—H str).

Example 6

The following example illustrates the coupling procedure of linkers 8 and 13 to form scFv constructs:

Tris(2-carboxyethyl)phosphine hydrochloride (TCEP) and monobromobimane (MBB) were purchased from Molecular Probes Inc. (Eugene, Oreg.). Protein scFv targeting the MUC-1 antigen was produced and purified as previously reported (see, Winthrop, M. D. et al. *Clin. Cancer Res.* 2003, 9, 3845S). SDS-Polyacrylamide Gel Electrophoresis (SDS-PAGE) gel was purchased from Pierce Biotechnology Inc. (Rockford, Ill.) and operated according to the manufacturer's directions. Protein bands were detected by CB staining and band intensities were measured by a S 1 Densitometer (Molecular Dynamics Inc., Sunnyvale, Calif.). The fluorescence intensities were measured by a Cary Eclipse Fluorescence spectrophotometer (Varian Inc., Palo Alto, Calif.). All other chemicals used were obtained from Sigma-Aldrich (St. Louis, Mo.).

Figure 2:
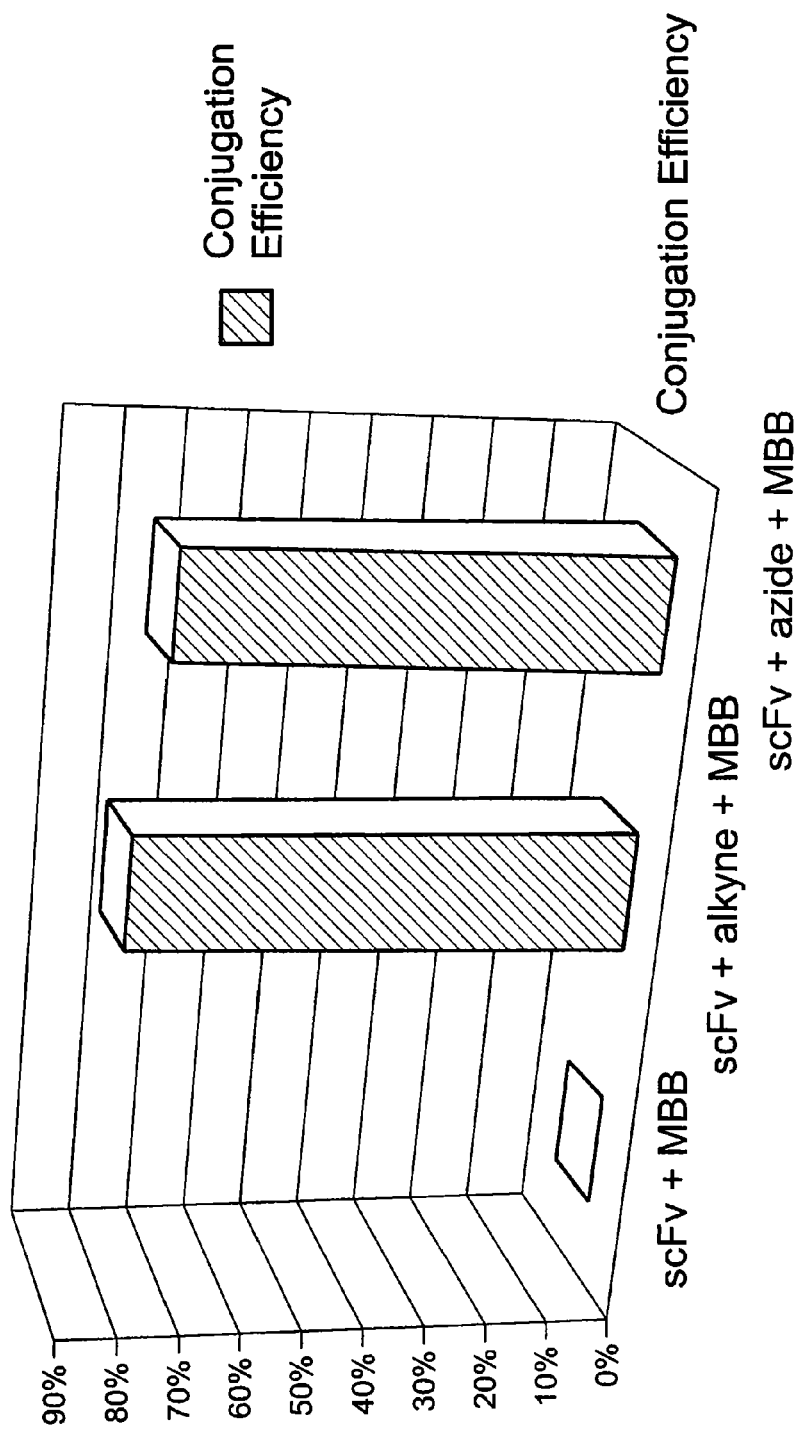
FIG. 2 provides a graph which shows the conjugation efficiency of a scFv to linkers 8 and 13.
Figure 3A:
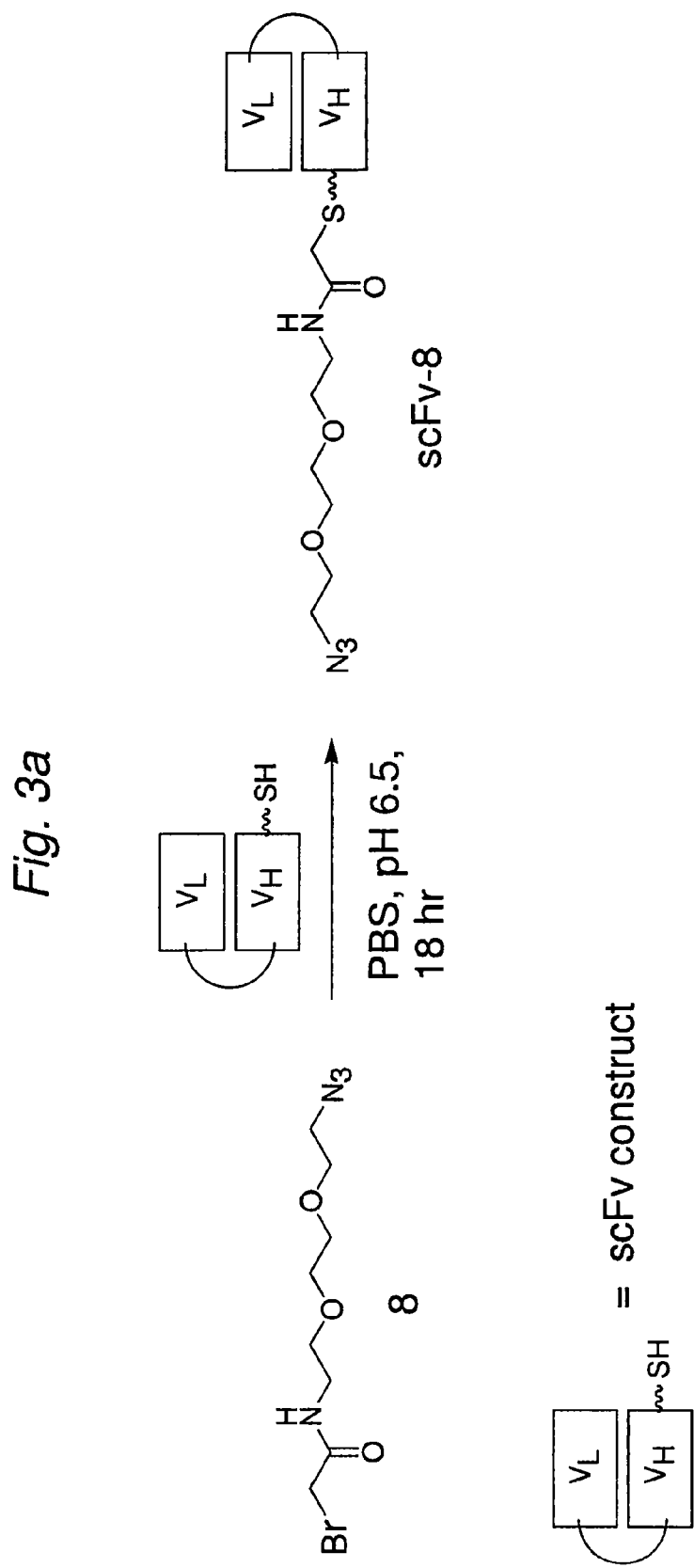
FIGS. 3A and 3B illustrate the conjugation reaction to connect linkers 8 and 13, respectively, to a scFv.
Figure 3B:
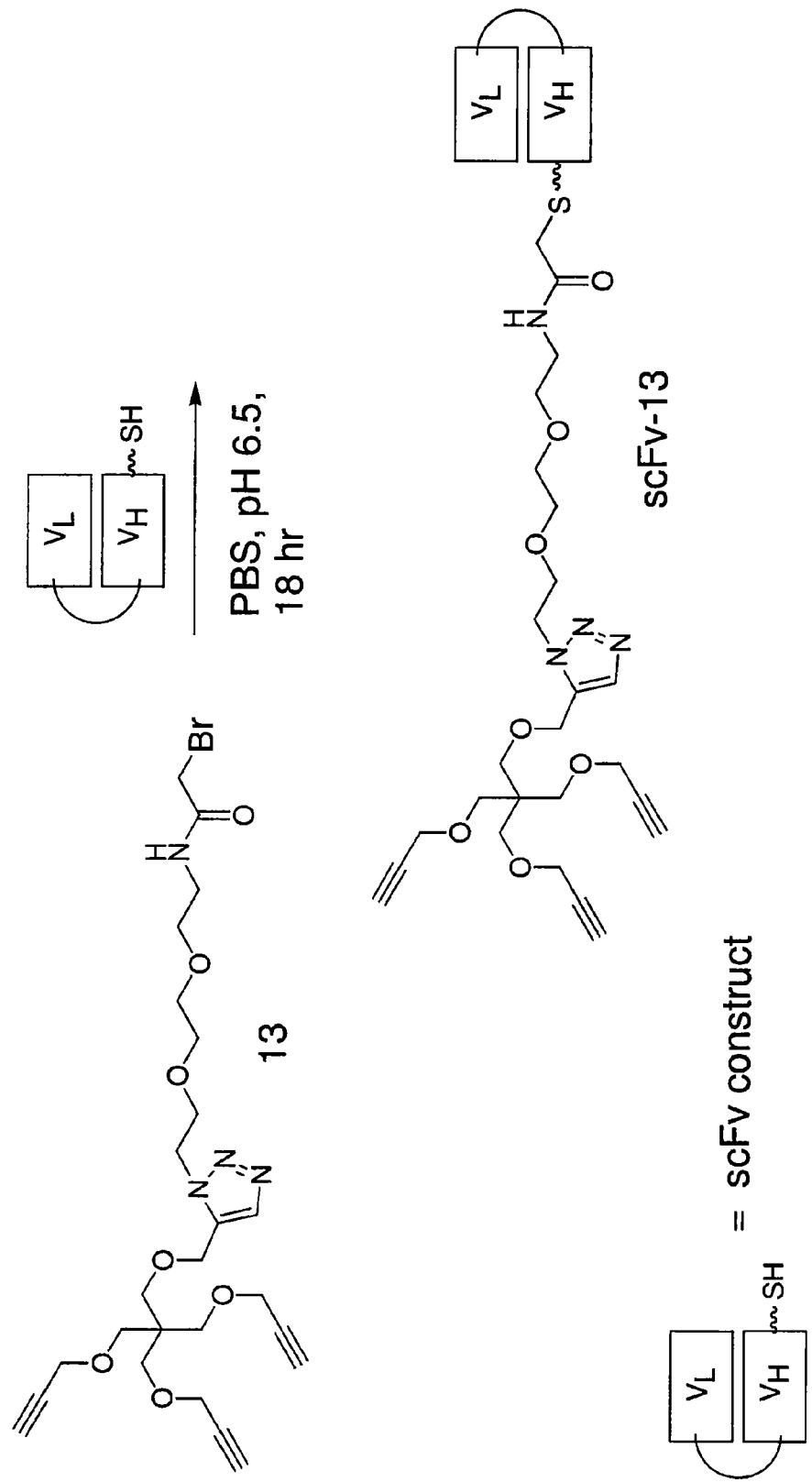

In two separated microtubes, protein scFv (2 nmoles, in 100 100 μL PBS) was pre-treated with TCEP. (4 nmoles, 2×) at pH 6.5 for 4 hr. Linkers 8 and 13 (10 nmoles of each) were added individually to separate microtubes. The reaction mixtures were incubated overnight at rt to form the conjugated products, scFv-8 and scFv-13 (see, FIGS. 3A and 3B). Un-conjugated linkers and TCEP were removed by 10 kDa cutoff membrane dialysis. Un-reacted cysteine was evaluated by reaction with monobromobimane (MBB) (see, Kosower, K. S. et al. *Methods Enzymol.* 1995, 251,133). The conjugation efficiency was determined by comparing the relative fluorescence intensities of scFv+linkers+MBB with scFv+MBB, assuming that MBB reacted with scFv in a quantitative manner. The conjugation efficiencies with linker 8 and linker 13 were 82% and 77% respectively (see, FIG. 2).

Example 7

The following example illustrates the ligation of a macromolecule comprising an alkynyl moiety, i.e., a scFv construct as described in Example 6 (scFv-5), to another macromolecule comprising an azido group, i.e., a scFv construct as described in Example 6 (i.e., scFv-8), to produce the divalent 1,2,3-triazole product. The 1,2,3-triazole product was formed in about ~30% yield.

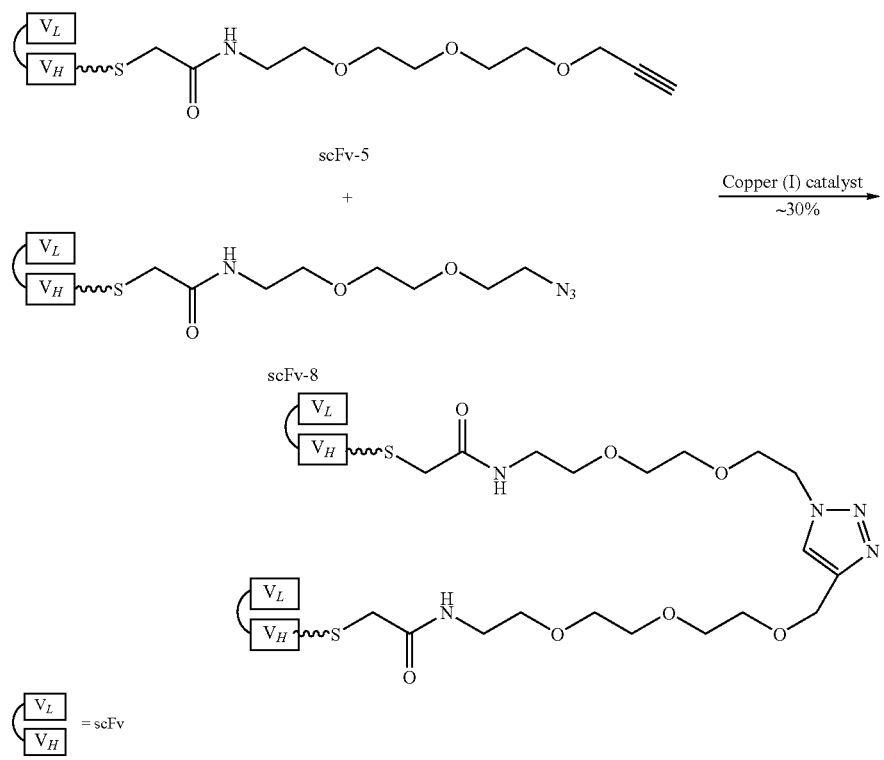

The modest yield observed in the reaction is attributed to the low concentration of the linking group attached to the reactive group moiety as compared to the antibody fragment itself (when one takes into account their difference in molecular weight), and to steric hinderance. By comparison, when a less sterically hindered azido group, i.e., a rhodamine azide 15 (see, Example 5), was used in place of scFv-8 in the above ligation reaction, the dipolar cycloaddition reaction proceeded efficiently to provide the desired 1,2,3-triazole product in higher yield.

A small ethylene glycol linker was selected to tether the azido or alkynyl moieties to the scFv fragments to minimized steric hindrance and increase solubility of the single chain fragments in aqueous solution.

Example 8

The following example illustrates the ligation of a macromolecule, i.e., a scFv as described in Example 6 (scFv-5) comprising an alkynyl moiety, to a di-azido compound 9 to produce the divalent 1,2,3-triazole product. The 1,2,3-triazole product was formed in modest yield.

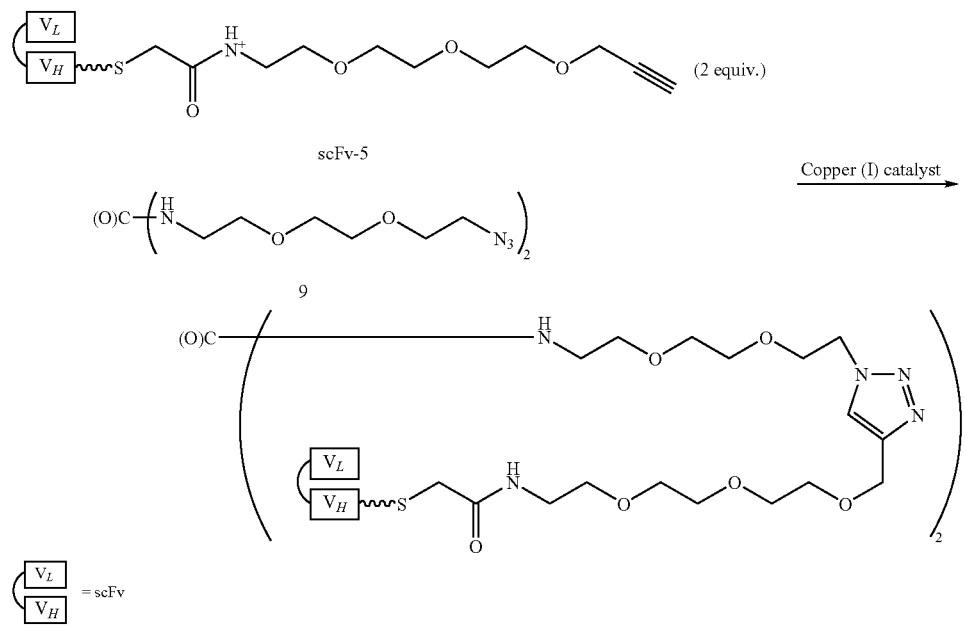

Example 9

Figure 4A:
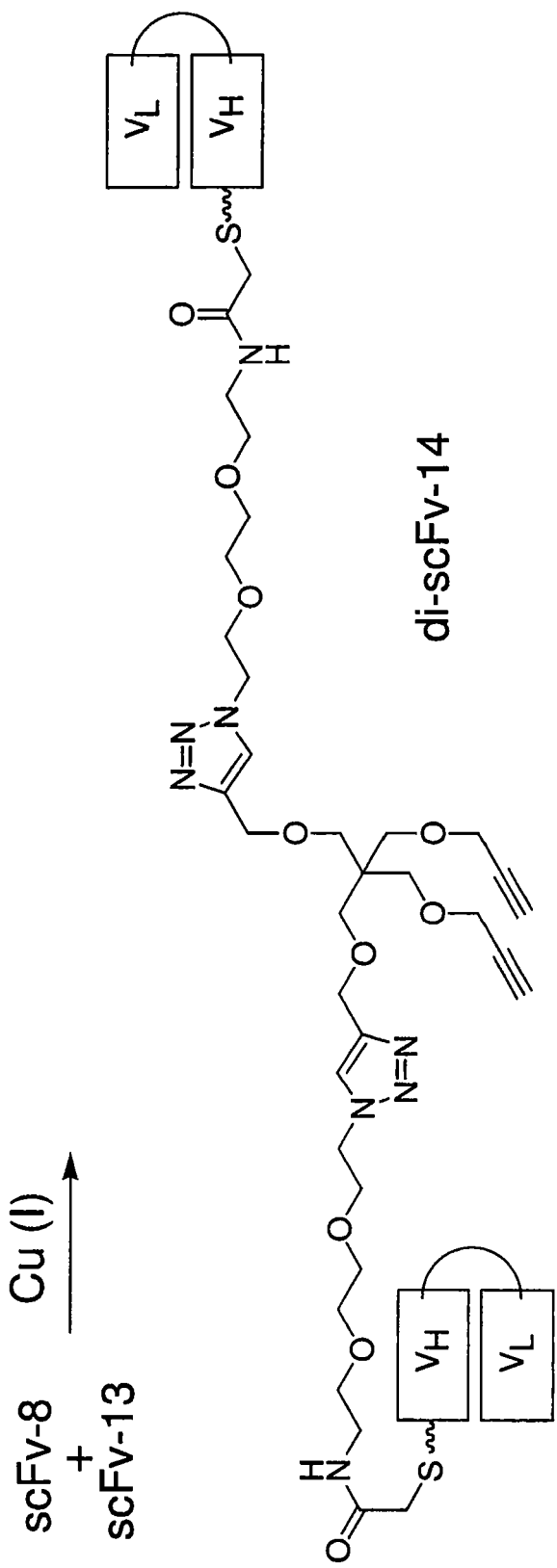
FIG. 4A illustrate the 1,3-dipolar cycloaddition reaction between scFv-8 and scFv-13.

The following illustrates an Alkyne-azide 1,3-dipolar cycloaddition reaction between scFv-8 and scFv-13 to form a multivalent scFv, i.e., di-scFv-14.

scFv-8 and scFv-13 were mixed together in a ratio of 1:1, 1:2 and 1:3. Tris[(1-benzyl-1H-1,2,3-triazol-4-yl)methyl] amine (TBTA) (5% molar ratio), $CuSO_4$ (5% molar ratio) and sodium ascorbate (10% molar ratio) were added sequentially. The reaction mixture was incubated at rt overnight. The desired di-scFv product, di-scFv-14, (see, FIG. 4A), having a molecular weight of 56 kDa was observed by SDS-PAGE (see, FIG. 4B, Lanes 1-3). It is noted, however, that varying the molar ratio of scFv-8 to scFv-13 does not significantly improve the conjugation efficiency. The conjugation efficiency in Lanes 0, 1, 2, and 3 are 0%, 58% (1:1 ratio), 74% (1:2 ratio) and 66% (1:3 ratio), respectively.

The ligated di-scFv mixture was purified by 10 kDa cut-off dialysis and concentrated by centriprep. The product was loaded (100 μg) on SDS-PAGE followed by CB staining (see, FIG. 4B). The band intensities were digitized from densitometry performed on the scanned gel images and protein standards as previously described (see, DeNardo, S. J. et al., *Bioconjugate Chem.* (2005), 251, 133) and presented in Table 1 (rows 1-3).

The yields of the products of the alkyne-azide 1,3-dipolar cycloaddition were calculated by the following equations and the results are shown on Table 1 (Rows 4-9):

Yields of 56 kDa $(Y_{56kDa}) = (R_{56kDa}/R_{tot})$

Yields of di-sulfide $(Y_{s-s}) = [R_{56kDa}(\text{Lane } 0)/R_{tot}(\text{Lane } 0)]$ Yields of 56 kDa from di-sulfide $(E_{s-s})$ = Free cysteine × $(Y_{s-s})$ Yields of 56 kDa from 1,3-dipolar Cycloaddition $(E_{56kDa}) = (Y_{56kDa}) \times [(1-(Es-s)]$ 1,3-Dipolar Cycloaddition Efficiency = $(E_{56kDa})$/conjugation efficiency

TABLE 1

| | | Lane 0 | Lane 1 | Lane 2 | Lane 3 |
|---|---|---|---|---|---|
| 1 | 56 kDa reading ($R_{56\ kDa}$) | 701.0 | 2180.0 | 5065.0 | 3985.0 |
| 2 | 32 kDa reading ($R_{28\ kDa}$) | 2275.0 | 1412.0 | 1430.0 | 1812.0 |
| 3 | Total reading ($R_{tot}$) | 2976.0 | 3592.0 | 6495.0 | 5797.0 |
| 4 | Yields of 56 kDa ($Y_{56\ kDa}$) | 24% | 61% | 78% | 69% |
| 5 | Yield of di-sulfide ($Y_{s-s}$) | 24% | 24% | 24% | 24% |
| 7 | Yields of 56 kDa from di-sulfide ($E_{s-s}$) | 24% | 5% | 5% | 5% |
| 8 | Yield of 56 kDa from 1,3-dipolar cycloaddition ($E_{56\ kDa}$) | 0% | 58% | 74% | 65% |
| 9 | 1,3-dipolar cycloaddition efficiency ($E_{CYC}$) | 0% | 73% | 94% | 83% |

Figure 4B:
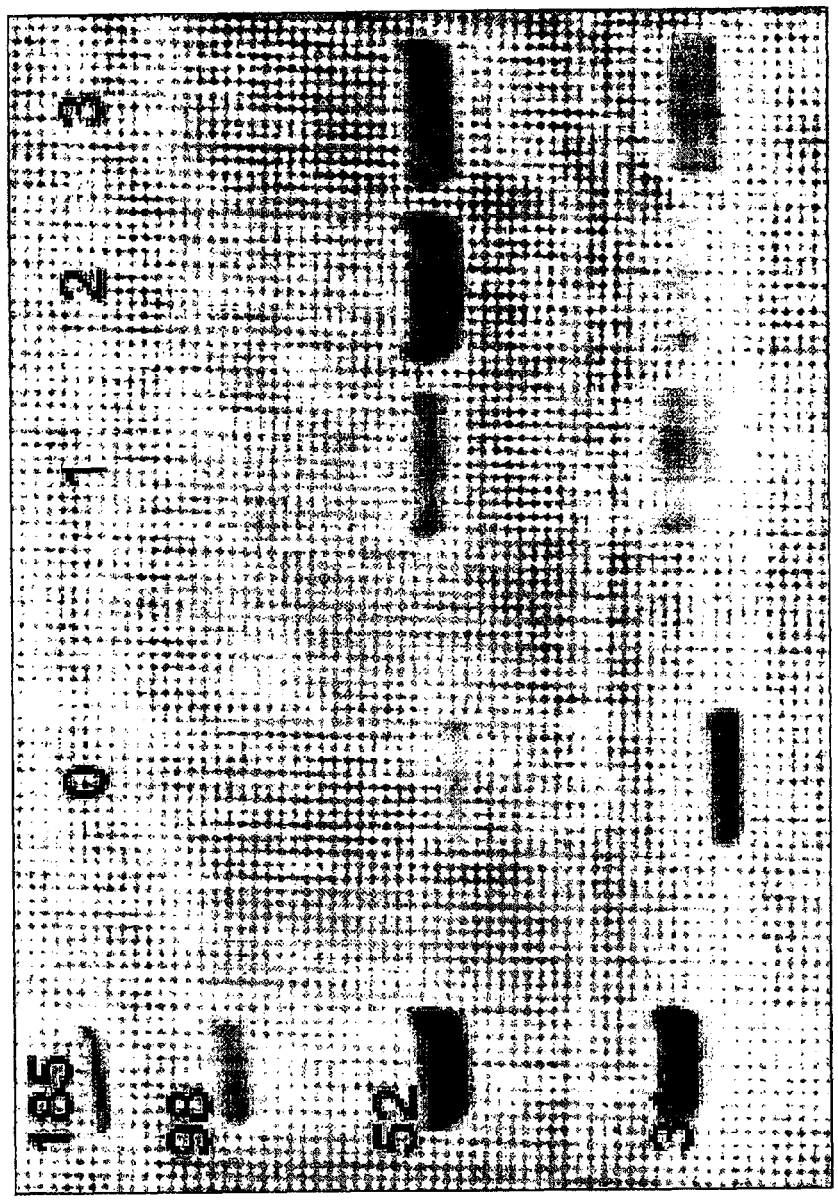
FIG. 4B illustrates the SDS-PAGE analysis of the alkyne-azide 1,3-dipolar cycloaddition reaction between scFv-8 and scFv-13. Lane 0 contains scFv only; Lanes 1-3 contains scFv-8 and scFv-13 in a 1:1, 1:2 and 1:3 molar ratio, respectively.
Figure 5:
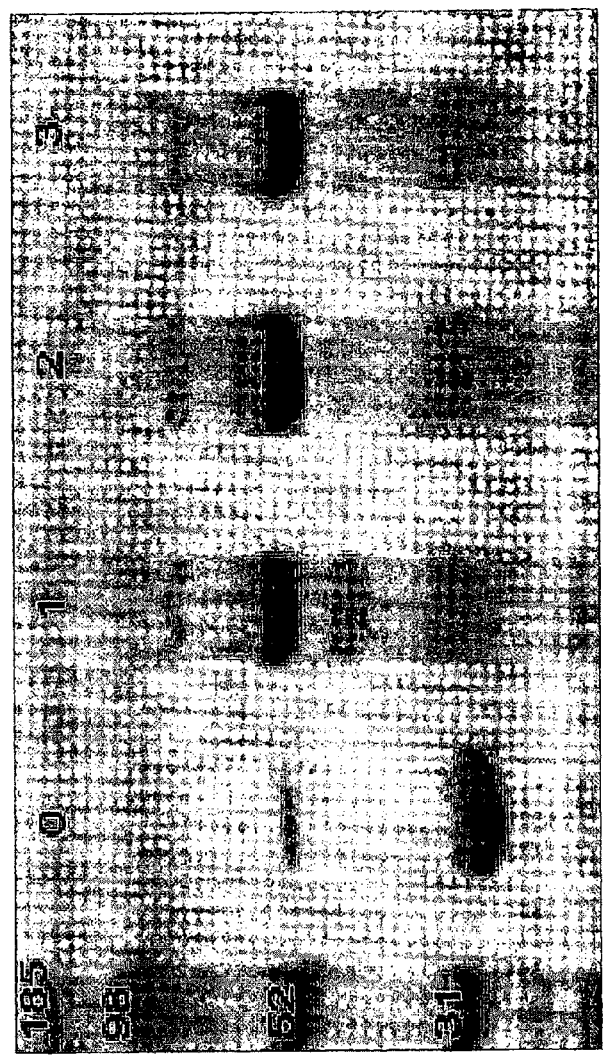
FIG. 5 illustrates SDS-PAGE analysis from the treatment of the observed 56 kDa product from the alkyne-azide 1,3-dipolar cycloaddition reaction (between scFv-8 and scFv-13) with a reducing agent (TCEP) in order to probe the structure of the 56 kDa product, i.e., to investigate the possibility that the observed 56 kDa band might the result of a disulfide formation between two scFVs.

To confirm that the observed product bands seen by SDS-PAGE (FIG. 4B) correspond to the product formed by the 1,3-dipolar cycloaddition and not by disulfide formation of unreacted scFv in the reaction mixture, the 56 kDa bands in FIG. 4B were treated with 5× tri(carboxyethyl)phosphine (TCEP), a reducing agent commonly used to break disulfide bonds and subject to SDS-PAGE. The results are shown in FIG. 5. In lane 0, which only contained scFv, any di-sulfide that formed was reduced back to the 28 kDa thiol (95%). However, the 56 kDa bands in lanes 1, 2, and 3, persisted even after treatment with the reducing agent (TCEP), which indicated that these bands correspond to the dipolar cycloaddition products and not disulfide compounds.

Figure 6:
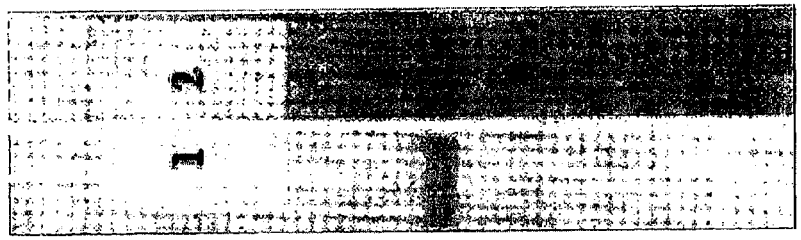
FIG. 6 illustrates the SDS-PAGE analysis of purified di-scFv-14 stained for protein (lane 1) and for polyethylene glycol (lane 2).

Further Purification of di-scFv-14 was accomplished by dialyzing the reaction mixture comprising di-scFv-14 with 10 kDa molecular weight cut-off membrane. After membrane purification, di-scFv-14 was further purified by Beckman coulter system Gold 128 Chromatography. Superdex-12 HR column (Amersham biosciences, CA) with PBS as elution solvents was performed at 0.5 mL per minute. UV absorbance was monitored simultaneously at 234 and 280 nm. Pure di-scFv-14 fractions were pooled and concentrated for further characterization by 4-12% SDS-PAGE (see, FIG. 6). The purified di-scFv-14 was stained for protein (lane 1) and polyethylene glycol (lane 2) (see, FIG. 6).

Example 10

The following example compares the binding affinity of a single monovalent scFv construct (26 kDa) versus the corresponding divalent construct (i.e., di-scFv-14) (52 kDa) against the MUC-1 peptide using ELISA. ELISA was performed on MUC-1 peptides, cell lysates and live cells. Ninety-six well plates were coated with the MUC-1 peptide (1 μg/100 μL/well) or DU145 cell lysates containing the cell membranes (100 μL per well). The latter was prepared as follows: Cell in log-phase were harvested and homogenized using a homogenizer. The concentration of cell lysates were adjusted to 1 mg protein per mL. For ELISA on live cells, cells in log-phase were harvested, re-suspended in fresh medium and added into flat 96-well plate (1×10⁶ cells per well). Medium was changed to BSA-PBS solution (PBS buffer containing 1.5% BSA). All reagents and washings were performed by spinning the cells at the bottom and by maintaining cell integrity. ELISA assays were performed in triplicate, following the approach described by Winthrop, M. D., et al., *Clin. Cancer Res.* 2003, 9, 3845S. In the ELISA studies, monovalent and divalent scFv binding effects were compared on synthetic MUC-1 peptide and DU145 cell lysates. The divalent scFv (di-scFv-14) show increased binding effects of 2-5 fold greater than the monovalent scFv (see, FIG. 7).

Example 11

The following example presents a comparison between the binding a monovalent scFv construct and the corresponding divalent construct (di-scFv-14) to the MUC-1 peptide located on cancer cells by immunohistochemistry (IHC).

Figure 8:
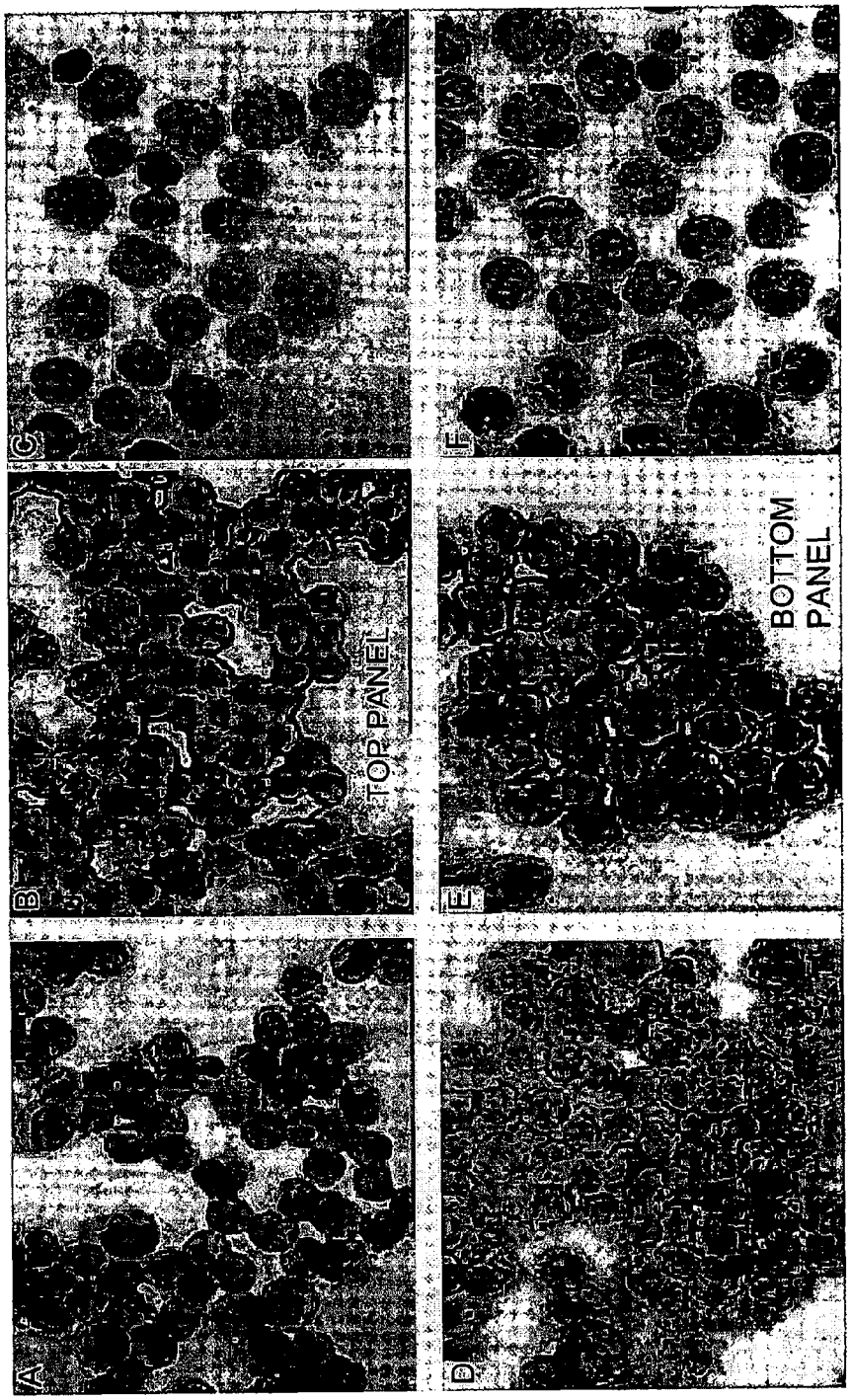
FIG. 8 illustrates the immunohistochemistry results of binding of di-scFv-14 to sections of human breast (MCF-7) and prostate tissue (DU145).

Formalin-fixed, human breast cancer cultured cells were smeared onto slides, air dried and fixed in 10% formalin. Endogenous peroxidase in cells was quenched by submerging slides in 0.3% $H_2O_2$ in methanol for 15 min. For fixed cells, antigen retrieval was performed using a microwave approach in sodium citrate buffer (10 mM, pH 6.0). After rinsing in PBS, all slides to be stained were blocked for 30 min with 10% goat serum in PBS. Monovalent scFv and the corresponding divalent scFv (di-scFv-14) proteins were separately added to corresponding slides followed by incubation for 3 hours at 37° C. After rinsing, HRP conjugated anti-E Tag antibody or HRP-conjugated anti-mouse IgG was added and incubated for one hour at room temperature followed by rinsing in PBS. The peroxidase reaction was developed with 3,3'-diaminobenzidine (DAB) reagent (Vector Laboratories, Burlingame, Calif.). After rinsing, sections were counterstained with Hematoxylin. Before photography, images of the slides were reviewed with a pathologist, Dr. Linlang Gun, photographed and electronically saved. Immunohistochemical staining of DU145 and MCF-7 cells (×650) were showed staining of the cells with the scFv and di-scFv. The brown membrane staining can be easily detected on the cells with monovalent scFv and divalent scFv proteins. The membranes of these tumor cells were strongly stained with di-scFv-14 (see, FIG. 8): Panel A: monovalent scFv bound to MCF-7; Panel D: di-scFv bound to MCF-7; Panel B: monovalent scFv bound to DU145; Panel E: di-scFv bound to DU145; Panel C: monovalent scFv does not bind to Jurkat cells; Panel F: di-scFv does not bind to Jurkat cells.

In all IHC experiments, Jurkat cells were used as negative control. IHC of the purified divalent scFv (i.e., di-scFv-14) on human prostate cancer cells (DU145) and human breast cancer cells (MCF-7) demonstrated that the divalent scFv had 2-4 times increased binding to cancer cells as compared to the monovalent scFv. The negative control (Jurkat lymphoma cells) did not stain.

Example 12

The following example illustrates the synthesis of 2,4,6-Tris-prop-2-ynyloxy-[1,3,5]triazine.

Preparation of
2,4,6-Tris-prop-2-ynyloxy-[1,3,5]triazine (16)

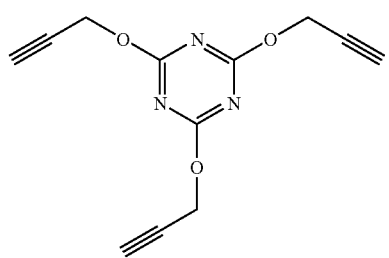

16

Cyanuric chloride (1.0 g, 5.42 mmol) was dissolved in 20 mL DCM, Prop-2-yn-1-ol (0.96 mL, 16.2 mmol), DIEA (2.7 ml, 16.2 mmol) was added to the solution. The mixture was stirred at room temperature for 18 h. The solvent was evaporated and the mixture was dissolved in DCM, washed with brine. Concentration afforded crude product which after further purification with silica gel chromatography (1:3 ethyl acetate:hexane), giving compound 16 1.26 g (95%). TLC (1:3 ethyl acetate:hexane): $R_f$=0.29. ¹H NMR (400 MHz, CDCl₃) δ 5.03 (6H, d, J=2.4 Hz), 2.53 (3H, t, J=2.4 Hz). ¹³C NMR (100 MHz, CDCl₃) δ 172.58, 77.08, 76.01, 56.05. Low-resolution mass spectrum (ESI) calcd. for $C_{12}H_{10}N_3O_3$ [M+H]⁺: 244.06. Found: 244.11.

Example 13

The following example illustrates the synthesis of 1,3,5-Tris-prop-2-ynyloxy-benzene.

Preparation of 1,3,5-Tris-prop-2-ynyloxy-benzene (17)

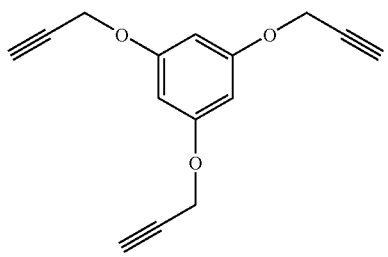

Trihydroxybenzene (0.5 g 3.08 mmol) and propargyl bromide (4 ml, 12 mmol) were dissolved in 10 mL THF, dry potassium carbonate (3.75 g, 12 mmol) and catalytic amount 18-crown-6-ether was added. The reaction mixture was stirred at room temperature for 18 h. The solvent was evaporated and the mixture was dissolved in DCM, washed with brine. Concentration afforded crude product which was further purified by silica gel chromatography (1:2 ethyl acetate:hexane), giving compounds 17 0.54 g (72%). TLC (1:2 ethyl acetate:hexane): $R_f$=0.36. $^1$H NMR (400 MHz, CDCl$_3$) δ 6.26 (3H, s), 4.64 (6H, d, J=2.4 Hz), 2.54 (3H, t, J=2.4 Hz). $^{13}$C NMR (100 MHz, CDCl$_3$) δ 159.41, 95.50, 78.35, 75.88, 56.04. Low-resolution mass spectrum (ESI) calcd. for C$_{15}$H$_{13}$O$_3$ [M+H]$^+$: 241.08. Found: 241.00.

What is claimed is:

1. A method of preparing a multivalent scFv, said method comprising:

(a) contacting a first scFv component having the formula:

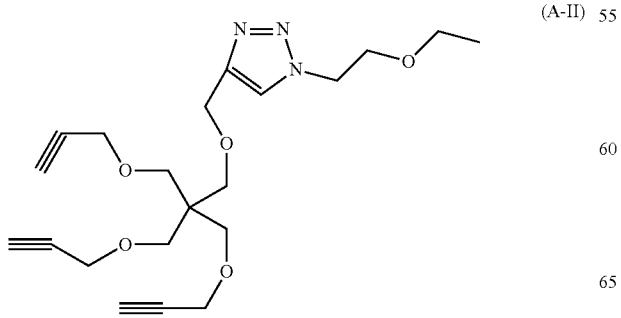

(A-II)

with a second scFv component having an attached linking group with a terminal azide moiety under conditions sufficient for 1,2,3-triazole formation to occur;

and optionally (b) attaching additional scFv components to the product of step (a) in a sequential manner by contacting the product of each step with another scFv component having an attached linking group with a terminal azide moiety under conditions sufficient for 1,2,3-triazole formation;

to produce said multivalent scFv.

2. A method of preparing a multivalent scFv, said method comprising:

(a) contacting a first scFv component having from one to eight attached alkyne moieties with a second scFv component having an attached linking group with a terminal azide moiety under conditions sufficient for 1,2,3-triazole formation to occur, wherein said second scFv component having an attached linking group with a terminal azide moiety has the formula:

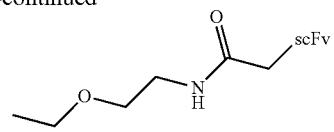

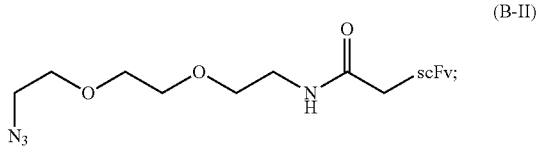

(B-II)

and optionally (b) attaching additional scFv components to the product of step (a) in a sequential manner by contacting the product of each step with another scFv component having an attached linking group with a terminal azide moiety under conditions sufficient for 1,2,3-triazole formation;

to produce said multivalent scFv.

3. A method of preparing a divalent scFv ("di-scFv"), said method comprising:
(a) contacting a first scFv component having the formula:

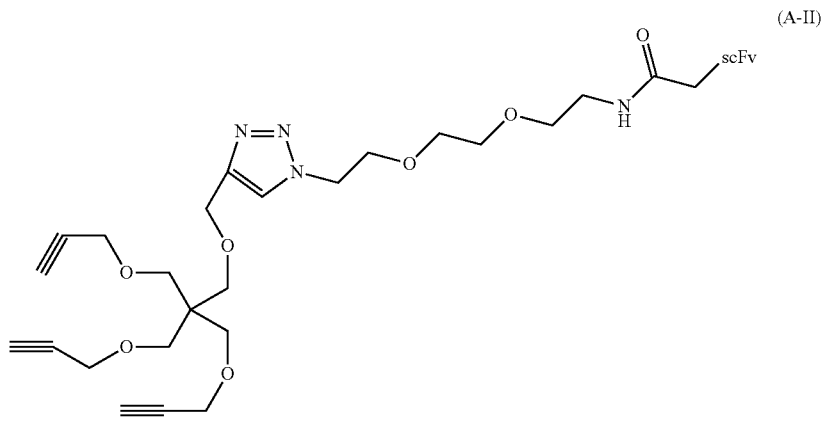
(A-II)

with a second scFv component having an attached linking group with a terminal azide moiety under conditions sufficient for 1,2,3-triazole formation to occur; and optionally (b) attaching additional scFv components to the product of step (a) in a sequential manner by contacting the product of each step with another scFv component having an attached linking group with a terminal azide moiety under conditions sufficient for 1,2,3-triazole formation;

to produce said di-scFv, wherein said di-scFv has the formula:

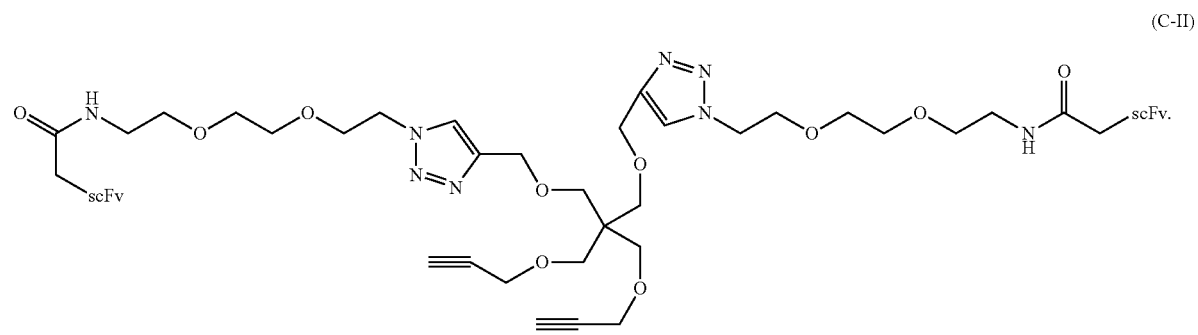
(C-II)

4. A method of covalently attaching two proteins to form a conjugate protein, said method comprising contacting a first protein component having the formula:

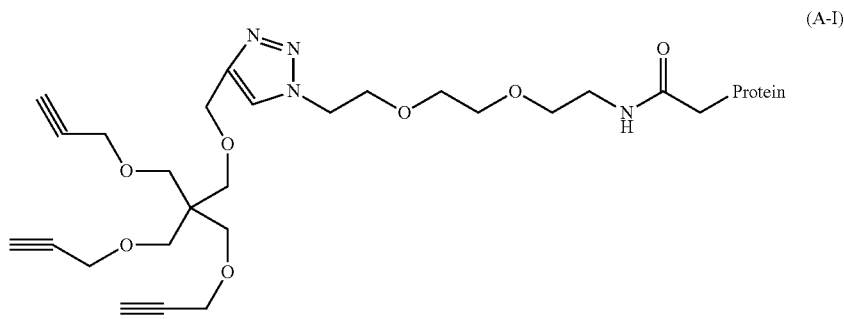
(A-I)

with a second protein component having an attached linking group with a terminal azide moiety under conditions sufficient for 1,2,3-triazole formation to occur and produce said conjugate protein.

5. A method of covalently attaching two proteins to form a conjugate protein, said method comprising contacting a first protein component having from one to eight attached alkyne moieties with a second protein component having an attached linking group with a terminal azide moiety under conditions sufficient for 1,2,3-triazole formation to occur and produce said conjugate protein, wherein said second protein component has the formula:

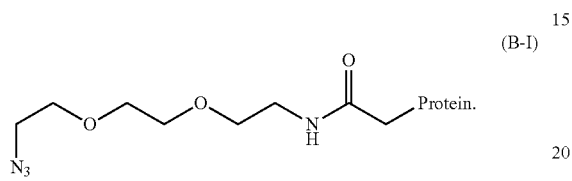

(B-I)

6. A method of covalently attaching two proteins to form a conjugate protein, said method comprising contacting a first protein component having the formula:

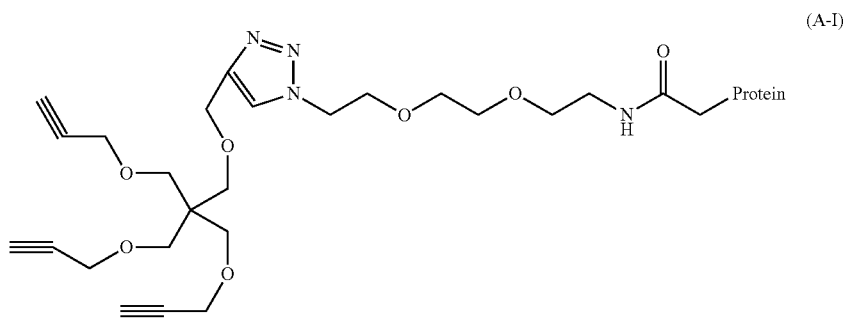

(A-I)

with a second protein component having an attached linking group with a terminal azide moiety under conditions sufficient for 1,2,3-triazole formation to occur and produce said conjugate protein, wherein said conjugate protein has the formula:

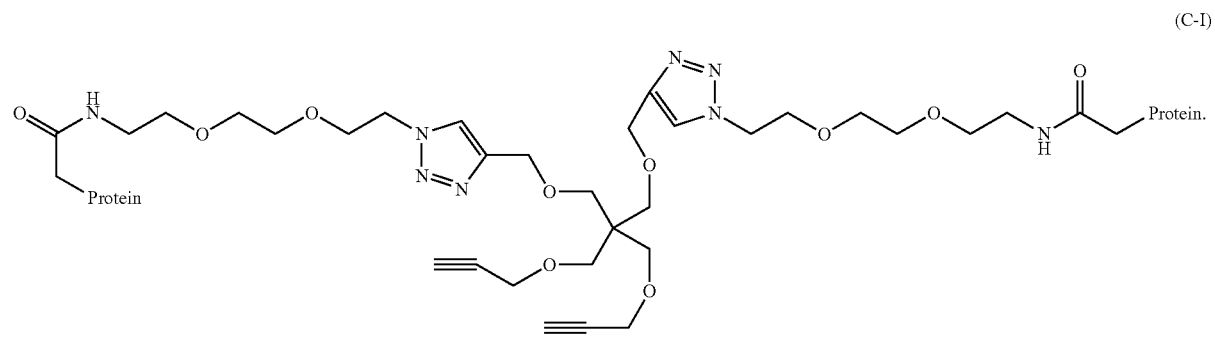

(C-I)

* * * * *